United States Patent
Hamm et al.

(10) Patent No.: US 9,572,794 B2
(45) Date of Patent: Feb. 21, 2017

(54) SUBSTITUTED INDOLES AS SELECTIVE PROTEASE ACTIVATED RECEPTOR 4 (PAR-4) ANTAGONISTS

(71) Applicant: Vanderbilt University, Nashville, TN (US)

(72) Inventors: Heidi E. Hamm, Nashville, TN (US); Shaun R. Stauffer, Nashville, TN (US); Craig W. Lindsley, Brentwood, TN (US); Wandong Wen, Nashville, TN (US); Summer E. Young, Nashville, TN (US); Matthew T. Duvernay, Nashville, TN (US); Kayla J. Temple, Antioch, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/820,488

(22) Filed: Aug. 6, 2015

(65) Prior Publication Data
US 2016/0083363 A1 Mar. 24, 2016

Related U.S. Application Data

(60) Provisional application No. 62/034,034, filed on Aug. 6, 2014.

(51) Int. Cl.
| | | |
|---|---|---|
| *A61K 31/404* | (2006.01) | |
| *A61K 31/407* | (2006.01) | |
| *A61K 31/437* | (2006.01) | |
| *C07D 209/10* | (2006.01) | |
| *C07D 209/30* | (2006.01) | |
| *C07D 239/00* | (2006.01) | |

(Continued)

(52) U.S. Cl.
CPC .......... *A61K 31/407* (2013.01); *A61K 31/404* (2013.01); *A61K 31/437* (2013.01); *A61K 31/4985* (2013.01); *A61K 31/5025* (2013.01); *A61K 31/519* (2013.01); *C07D 209/10* (2013.01); *C07D 209/30* (2013.01); *C07D 221/00* (2013.01); *C07D 237/00* (2013.01); *C07D 239/00* (2013.01); *C07D 401/04* (2013.01); *C07D 513/04* (2013.01); *C08L 67/02* (2013.01); *C08L 69/00* (2013.01); *C08L 2205/02* (2013.01)

(58) Field of Classification Search
CPC .. A61K 31/404; A61K 31/407; A61K 31/437; A61K 31/4985; A61K 31/5025; A61K 31/519; C07D 209/10; C07D 209/30; C07D 221/00; C07D 237/00; C07D 239/00; C07D 241/00
USPC ........................................ 514/339
See application file for complete search history.

(56) References Cited

U.S. PATENT DOCUMENTS 6,787,651 B2 * 9/2004 Stolle ................... A61K 31/404
544/143

OTHER PUBLICATIONS

Wen et al, Bioorganic & Medicinal Chemistry Letters 24 (2014), pp. 4708-4713.*

(Continued)

*Primary Examiner* — Kamal Saeed
*Assistant Examiner* — Janet L Coppins
(74) *Attorney, Agent, or Firm* — Stites & Harbison PLLC; Richard S. Myers, Jr.

(57) ABSTRACT

Embodiments of the invention include substituted indole compounds and compositions thereof to inhibit protease activated receptor-4. Also described are methods of preparation of compositions and methods for treating diseases related to thrombotic disorders by administration of the composition.

27 Claims, 1 Drawing Sheet

(51) Int. Cl.
   C07D 401/04    (2006.01)
   C07D 513/04    (2006.01)
   A61K 31/4985   (2006.01)
   A61K 31/519    (2006.01)
   A61K 31/5025   (2006.01)
   C07D 221/00    (2006.01)
   C07D 237/00    (2006.01)
   C08L 67/02     (2006.01)
   C08L 69/00     (2006.01)

(56) References Cited

OTHER PUBLICATIONS

CAPLUS abstract of Gabrielyan, G and Papayan, G, Armyanskii Khimicheskii Zhurnal (1979), vol. 32(4), pp. 309-314.*
Ruggeri, Z.M. Platelets in atherothrombosis. Nat. Med. 2002, 8, 1227-1234.
Adams, M. N.; Ramachandran, R.; Yau, M.-K; Suen, J. Y.; Fairlie, D. P.; Hollenberg, M. D.; Hooper, J. D. Pharm. Therap. 2011, 130, 248-282.
Coughlin, S. Nature 2000, 407, 258-322.
Kahn, M. L.; Zheng, Y. W.; Huang, W.; Bigornia, V.; Zeng, D.; Moff, S.; Farese, R. V., Jr.; Tam, C.; Coughlin, S. R. Nature 1998, 394, 690-694.
Mao, Y.; Zhang, M.; Tuma, R.; Kunapuli, S. Journal of cerebral blood flow and metabolism 2010, 30, 1044-1096.
Vandendries, E. R.; Hamilton, J. R.; Coughlin, S. R.; Furie, B.; Furie, B. C. Proc. Nat. Acad. Sci. USA 2007, 104, 288-292.
Cornelissen, I.; Palmer, D.; David, T.; Wilsbacher, L.; Concengco, C.; Conley, P.; Pandey, A.; Coughlin, S. R. Proc. Nat. Acad. Sci. USA 2010, 107, 18605-18615.
Sambrano, G.; Weiss, E.; Zheng, Y.; Huang, W.; Coughlin, S. Nature 2001, 413, 7 4-82.
Henrih-Noack, P.; Riek-Burchardt, M.; Baldauf, K.; Reiser, G.; Reymann, K. Brain Research 2006, 1070, 232-273.
See http://www.mercknewsroom.com and http://www.fda.gov for May 2014 Zontivity™ press releases.
For information on the MLPCN and information on how to request probe compounds, such as ML354, see: http://mli.nih.gov/mli/mlpcn/.
Lee, F.-Y.; Lien, J.-C.; Huang, L.-J.; Huang, T.-M.; Tsai, S.-C.; Teng, C.-M.; Wu, C.-C.; Cheng, F.-C.; Kuo, S.-C. J. Med. Chem. 2001, 44, 3746-3755.
Chen, H.-S.; Kuo, S.-C.; Teng, C.-M.; Lee, F.-Y.; Want, J.-P.; Lee, Y.-C.; Kuo, C.-W.; Huang, C.-C.; Wu, C.-C.; Huang, L.-J. Bioorg. Med. Chem. 2008, 16, 1262-1340.
Young, S. E.; Duvemay, M. T.; Schulte, M. L.; Lindsley, C. W.; Hamm, H. E. PLoS One 2013, 8, e65528.
Smith, G. F. Progress in Medicinal Chemistry 2011, 50, 1-47.
Kou-San, J. Microbiology and Molecular Biology Reviews 2012, 74, 250-272.
Cai, Q.; Li, Z.; Wei, J.; Ha, C.; Pei, C.; Ding, K. Chem. Commun. 2009, 7581-7583.
Meanwell, N. A. J. Med. Chem. 2011, 54, 2529-2591.
Duvemay, et al., Protease-Activated Receptor (PAR) 1 and PAR4 Differentially Regulate Factor V Expression from Human Plateletss; Mol Pharmacol, Apr. 2013, 83:781-792.
Wen, et al., Substituted indoles as selective protease activated receptor 4 (PAR-4) antagonists: Discovery and SAR of ML354; Bioorganic & Medicinal Chemistry Letters 24 (2014) 4708-4713.

* cited by examiner

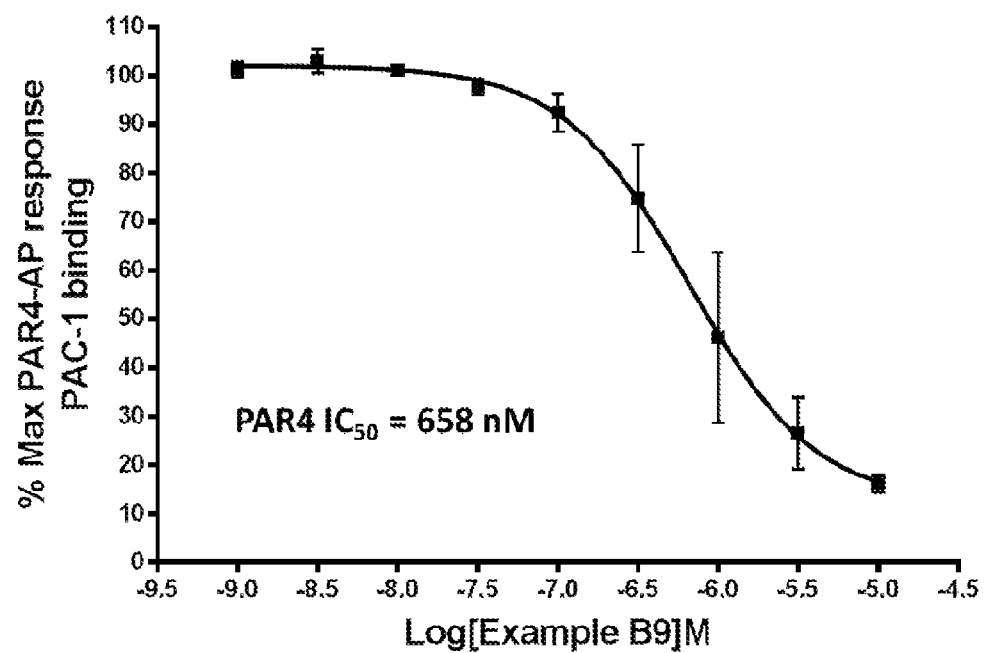

SUBSTITUTED INDOLES AS SELECTIVE PROTEASE ACTIVATED RECEPTOR 4 (PAR-4) ANTAGONISTS

GOVERNMENT SUPPORT

This invention was made with support from grants from the National Institutes of Health grants nos. U54MH084659 and 1R01NS081669. The United States Government has certain rights to this invention.

FIELD OF THE INVENTION

Embodiments of the present invention relate to novel indoles as selective protease activated receptor 4 (PAR4) antagonists. The compounds of the present invention are useful in preventing or treating thromboembolic disorders. Other embodiments of the present invention relate to pharmaceutical compositions containing the compounds of the present invention as well as methods of using the same.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharide factor Xa inhibitors, direct thrombin inhibitors such as Bivalirudin, and antiplatelet agents such as integrin αIIbβ3 inhibitors, aspirin, clopidogrel (PLAVIX®), and vorapaxar (Zontivity®). Additionally, current anti-platelet therapies have limitations including increased risk of bleeding as well as partial efficacy (relative cardiovascular risk reduction in the 20 to 30% range). Thus, there is an unmet medical need for safe and efficacious oral or parenteral antithrombotics for the prevention and treatment of a wide range of thromboembolic disorders.

Thrombin is a protease at the center of coagulation. In addition to the activation of coagulation factors and fibrinogen, thrombin regulates cellular activities through stimulation of the G-protein coupled protease activated receptors (PARs). These receptors are activated by cleavage by thrombin, and in a unique mechanism, the new amino terminus is the activating "tethered ligand." This causes irreversible activation of the receptors. Platelets express two PARs, PAR-1 and PAR4. PAR-1 is ubiquitously expressed and PAR1 signaling underlies various conditions including coagulation, inflammation, nociception, healing and cancer metastasis. Conversely PAR4 expression is constrained, mainly to platelets and expression in certain brain areas and vascular beds after stress.

PAR1 is the "high affinity" thrombin receptor requiring little thrombin for activation whereas PAR4 is the low affinity thrombin receptor and requires significantly higher amounts of thrombin for activation. Due to this difference in affinity, PAR1 and PAR4 are engaged in a progressive manner, with PAR1 activated at low thrombin concentrations and PAR4 activated at higher thrombin concentrations. Because of the delay in activation we hypothesize that PAR4 antagonism might not affect hemostasis as potently and thus may be a better therapeutic target than PAR1.

Inhibitors of PAR1 have been investigated extensively, and several compounds, including vorapaxar and atopaxar have advanced into late stage clinical trials. Recently, in the TRACER phase III trial among non-ST-segment elevation acute coronary syndromes (ACS) patients, vorapaxar did not significantly reduce the primary composite endpoint, and in fact was halted early due to a significant increase in the risk of major bleeding, including intracranial hemorrhage (Tricoci, P. et al, *N. Eng. J Med.*, 366(1):20-33 (2012). However, among non-ST-segment ACS patients undergoing CABG specifically, vorapaxar was associated with a significant reduction in ischemic events and no significant increase in major CABG-related bleeding (Whellan D J et al, *J Am Coll Cardiol.*, 63(11): 1048-57(2014). The TRA 2P-TIMI 50 trial demonstrated that in patients with myocardial infarction, vorapaxar reduced the risk of cardiovascular death or ischemic events with a significant increase in moderate to severe bleeding when added to the standard anti-platelet therapy (Scirica B M et al, *Lancet.*, 380(9850): 1317-24 (2012). Similar results were collected among patients with peripheral artery disease demonstrating significant beneficial effects on limb ischemia and peripheral revascularization with increased risk of bleeding (Bonaca M P et al, Circulation., 127(14): 1522-9 (2013). However, among patients with prior ischemic stroke adding vorapaxar to the standard of care increased the risk of intracranial hemorrhage without improvement in major vascular events (Morrow D A et al, *Stroke* 44(3):691-8 (2013). Although the PAR1 antagonist Vorapaxar (Zontivity™) was approved by the FDA as the first in class protease activated receptor antagonist, its potential application is severely limited by the bleeding side effects and increased risk of hemorrhagic stroke.

Interestingly, PAR4-/- mice are protected from thrombosis and cerebral ischemia-reperfusion injury and have prolonged tail bleeding times but no bleeding disorder. Since PAR4, is the low affinity thrombin receptor, Previous worksuggests that PAR4 would not be engaged until later stages of hemostasis, and possibly thrombosis. Thus PAR4 is an attractive target for a safer anti-platelet therapy for the treatment or prevention of thrombosis and cerebrovascular injury because inhibition of PAR4 preserves PAR1 as well as thromboxane, and purinergic receptor signaling which are major mediators of platelet activation. Therefore hemostasis is likely to be left intact and potential bleeding side effects could be ameleiorated or eliminated entirely.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", *J. Med. Chem.*, 44(22):3746-3749 (2001) discloses in the abstract that the compound:

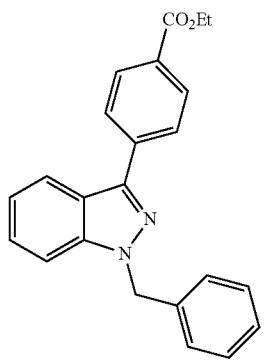

YD-3

"was found to be a selective and potent inhibitor or protease-activated receptor type 4 (PAR4)-dependent platelet activation."

YD-3 was also referenced in Wu, C-C. et al, "Selective Inhibition of Protease-activated Receptor 4-dependent Platelet Activation by YD-3", Thromb. Haemost., 87: 1026-1033 (2002). Also, see Chen, H. S. et al, "Synthesis and platelet activity", J. Bioorg. Med. Chem., 16: 1262-1278 (2008).

EP1166785 A1, EP0667345, and WO 2013/163279, all incorporated herein by reference, disclose various compounds which are useful as inhibitors of platelet aggregation.

SUMMARY OF THE INVENTION

The present inventors have discovered that indole compounds of the present invention are PAR4 antagonists, which inhibit platelet aggregation.

Accordingly, the present invention provides novel substituted indole analogues that are PAR4 antagonists and are useful as selective inhibitors of platelet aggregation, including stereoisomers, tautomers, pharmaceutically acceptable salts, solvates, or prodrug esters thereof.

In accordance with the purpose(s) of the invention, as embodied and described herein, the invention, in one aspect, relates to compounds useful as protease activated receptor-4 (PAR4) antagonists, methods of making same, pharmaceutical compositions comprising same, and methods of treating disorders associated with PAR4 activity. Further disclosed are methods and pharmaceutical compositions useful for treating a disease related to PAR4 activity.

Embodiments of the present invention relate to compounds and compositions that are PAR4 antagonists. Compounds and compositions of the present invention are also useful in preventing and treating thromboembolic disorders, including arterial thrombosis.

The present invention also relates to pharmaceutical compositions that include compounds of the present invention, and methods of using compounds and compositions of the present invention.

Other embodiments of the present invention include compounds derived from an indole-based Protease Activated Receptor-4 (PAR4) antagonist scaffold.

Included in the present invention are pharmaceutical compositions comprising a pharmaceutically acceptable carrier and at least one of the compounds of the present invention or stereoisomers, tautomers, pharmaceutically acceptable salts, solvates, or prodrug esters thereof.

Another embodiment of the present invention is a method for the treatment or prophylaxis of thrombosis, and/or thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrug esters thereof.

Another embodiment of the present invention are the compounds described herein or or stereoisomers, tautomers, pharmaceutically acceptable salts, solvates, or prodrug esters thereof, for use in therapy.

Another embodiment of the present invention is the use of the compounds of the present invention or stereoisomers, tautomers, pharmaceutically acceptable salts, solvates, or prodrug esters thereof, for the manufacture of a medicament for the treatment or prophylaxis of a thromboembolic disorder.

Other embodiments of the invention will be apparent from the following detailed description and claims.

BRIEF DESCRIPTION OF THE DRAWINGS

FIG. 1 is a graph that shows an example concentration response curve (CRC) measuring antagonism of PAR4 mediated $\alpha_{IIb}\beta 3$ activation via PAC-1 binding using Example B9.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

One embodiment of the present invention is indole compounds, stereoisomers, tautomers, salts, solvates, or prodrugs thereof, of formula (I), having the structure:

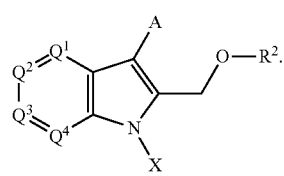

wherein:
$Q^1$ is selected from N and $CR^{1a}$;
$Q^2$ is selected from N and $CR^{1b}$, or can optionally cyclize with $Q^3$ to form a C5 or C6 saturated heterocycle;
$Q^3$ is selected from N and $CR^{1c}$, or can optionally cyclize with $Q^2$ to form a C5 or C6 saturated heterocycle;
$Q^4$ is selected from N and $CR^{1d}$; and wherein 0, 1, or 2 of $Q^1$, $Q^2$, $Q^3$, and $Q^4$ are N;
$R^{1a}$, $R^{1b}$, $R^{1c}$, and $R^{1d}$, when present, are each independently selected from hydrogen, halogen, hydroxyl, cyano, $C_1$-$C_3$ alkyl sulfone, $C_1$-$C_3$ polyhaloalkyl sulfone, $C_1$-$C_6$ alkyl, $C_1$-$C_6$ haloalkyl, $C_1$-$C_6$ polyhaloalkyl, $C_1$-$C_6$ alkoxy, $(C_1$-$C_6)$alkoxy-$(C_1$-$C_6)$alkyl, $(C_1$-$C_6)$alkylamino, $(C_1$-$C_6)$haloalkyl-oxy-$(C_1$-$C_6)$alkyl, $(C_1$-$C_6)$polyhaloalkyl-oxy-$(C_1$-$C_6)$alkyl, $(C_1$-$C_6)$polyhaloalkyl-$(C_1$-$C_6)$alkoxy, and $(C_1$-$C_6)$ dialkylamino; n is 0-5;
X is independently selected from optionally substituted $CH_2$-aryl, $CH_2$-heteroaryl, $CH_2$-biaryl, or

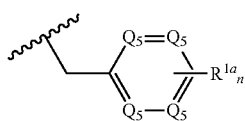

wherein:

$Q^5$ is selected from N, $CR^{1a}$, and $R^{1a}$; and n is 0-5;

$R^2$ is selected from hydrogen, $C_1$-$C_3$ alkyl, $C_1$-$C_3$ haloalkyl, and $C_1$-$C_3$ polyhaloalkyl, $(C_1$-$C_3)$polyhaloalkyl-oxy-$(C_1$-$C_3)$alkyl, and $(C_1$-$C_3)$haloalkyl-oxy-$(C_1$-$C_3)$alkyl, and A is optionally substituted and chosen from aryl or heteroaryl;

or a pharmaceutically acceptable salt, solvate, or polymorph thereof.

Also disclosed are pharmaceutical compositions that comprise a compound described herein or pharmaceutically acceptable salt, solvate, or polymorph thereof, and a pharmaceutically acceptable carrier. In one embodiment, the composition includes a compound having a structure represented by formula (I):

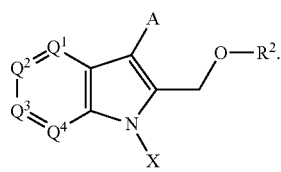

I wherein:

$Q^1$ is selected from N and $CR^{1a}$;

$Q^2$ is selected from N and $CR^{1b}$, or can optionally cyclize with $Q^3$ to form a C5 or C6 saturated heterocycle;

$Q^3$ is selected from N and $CR^{1c}$, or can optionally cyclize with $Q^2$ to form a C5 or C6 saturated heterocycle;

$Q^4$ is selected from N and $CR^{1d}$; and wherein 0, 1, or 2 of $Q^1$, $Q^2$, $Q^3$, and $Q^4$ are N;

$R^{1a}$, $R^{1b}$, $R^{1c}$, and $R^{1d}$, when present, are each independently selected from hydrogen, halogen, hydroxyl, cyano, $C_1$-$C_3$ alkyl sulfone, $C_1$-$C_3$ polyhaloalkyl sulfone, $C_1$-$C_6$ alkyl, $C_1$-$C_6$ haloalkyl, $C_1$-$C_6$ polyhaloalkyl, $C_1$-$C_6$ alkoxy, $(C_1$-$C_6)$alkoxy-$(C_1$-$C_6)$alkyl, $(C_1$-$C_6)$alkylamino, $(C_1$-$C_6)$haloalkyl-oxy-$(C_1$-$C_6)$alkyl, $(C_1$-$C_6)$polyhaloalkyl-oxy-$(C_1$-$C_6)$alkyl, $(C_1$-$C_6)$polyhaloalkyl-$(C_1$-$C_6)$alkoxy, and $(C_1$-$C_6)$dialkylamino; n is 0-5;

X is independently selected from optionally substituted $CH_2$-aryl, $CH_2$-heteroaryl, $CH_2$-biaryl, or

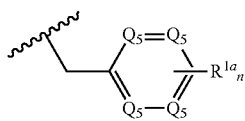

wherein:

$Q^5$ is selected from N, $CR^{1a}$, and $R^{1a}$; and n is 0-5;

$R^2$ is selected from hydrogen, $C_1$-$C_3$ alkyl, $C_1$-$C_3$ haloalkyl, and $C_1$-$C_3$ polyhaloalkyl, $(C_1$-$C_3)$polyhaloalkyl-oxy-$(C_1$-$C_3)$alkyl, and $(C_1$-$C_3)$haloalkyl-oxy-$(C_1$-$C_3)$alkyl, and A is optionally substituted and chosen from aryl or heteroaryl;

or a pharmaceutically acceptable salt, solvate, or polymorph thereof, and a pharmaceutically acceptable carrier.

Also disclosed are the pharmaceutical compositions described above, further comprising at least one additional drug or therapeutic agent. In certain embodiments of the preset invention, the at least one additional therapeutic agent(s) are an anti-platelet agent or a combination thereof. Examples of the anti-platelet agents include P2Y12 antagonists and/or aspirin. Preferably, the P2Y12 antagonists are clopidogrel, ticagrelor, or prasugrel. In another embodiment, the at least one additional therapeutic agent is an anticoagulant. Examples of the anticoagulant agent include FXa inhibitors or thrombin inhibitors. The FXa inhibitors may be, for example, apixaban or rivaroxaban. The thrombin inhibitor may be, for example, dabigatran.

Also disclosed herein are methods for the treatment of a disease state associated with PAR4 activity in a mammal comprising the step of administering to the mammal at least one compound in a dosage and amount effective to treat the disease state, the compound having a structure represented by formula (I):

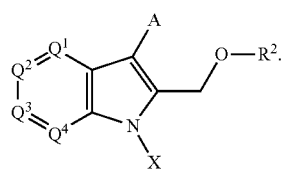

I wherein:

$Q^1$ is selected from N and $CR^{1a}$;

$Q^2$ is selected from N and $CR^{1b}$, or can optionally cyclize with $Q^3$ to form a C5 or C6 saturated heterocycle;

$Q^3$ is selected from N and $CR^{1c}$, or can optionally cyclize with $Q^2$ to form a C5 or C6 saturated heterocycle;

$Q^4$ is selected from N and $CR^{1d}$; and wherein 0, 1, or 2 of $Q^1$, $Q^2$, $Q^3$, and $Q^4$ are N;

$R^{1a}$, $R^{1b}$, $R^{1c}$, and $R^{1d}$, when present, are each independently selected from hydrogen, halogen, hydroxyl, cyano, $C_1$-$C_3$ alkyl sulfone, $C_1$-$C_3$ polyhaloalkyl sulfone, $C_1$-$C_6$ alkyl, $C_1$-$C_6$ haloalkyl, $C_1$-$C_6$ polyhaloalkyl, $C_1$-$C_6$ alkoxy, $(C_1$-$C_6)$alkoxy-$(C_1$-$C_6)$alkyl, $(C_1$-$C_6)$alkylamino, $(C_1$-$C_6)$haloalkyl-oxy-$(C_1$-$C_6)$alkyl, $(C_1$-$C_6)$polyhaloalkyl-oxy-$(C_1$-$C_6)$alkyl, $(C_1$-$C_6)$polyhaloalkyl-$(C_1$-$C_6)$alkoxy, and $(C_1$-$C_6)$dialkylamino; n is 0-5;

X is independently selected from optionally substituted $CH_2$-aryl, $CH_2$-heteroaryl, $CH_2$-biaryl, or

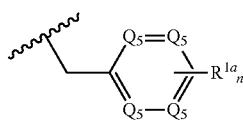

wherein:

$Q^5$ is selected from N, $CR^{1a}$, and $R^{1a}$; and n is 0-5;

$R^2$ is selected from hydrogen, $C_1$-$C_3$ alkyl, $C_1$-$C_3$ haloalkyl, and $C_1$-$C_3$ polyhaloalkyl, $(C_1$-$C_3)$polyhaloalkyl-oxy-$(C_1$-$C_3)$alkyl, and $(C_1$-$C_3)$haloalkyl-oxy-$(C_1$-$C_3)$alkyl, and A is optionally substituted and chosen from aryl or heteroaryl;

or a pharmaceutically acceptable salt, solvate, or polymorph thereof.

Also disclosed are methods for making a compound comprising the steps of providing an indole compound having a structure represented by formula (I):

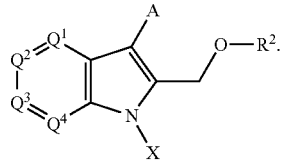

as shown in the Examples below, and wherein the variable are defined herein.

Also disclosed are the products of the disclosed methods of making.

Also disclosed are pharmaceutical compositions that comprise the products of the compounds disclosed herein.

Also disclosed are methods for the manufacture of a medicament for antagonizing PAR4 activity in a mammal comprising combining a compound having a structure represented by formula (I):

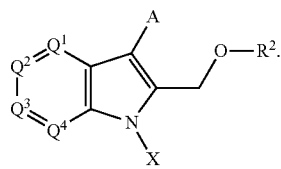

wherein:

$Q^1$ is selected from N and $CR^{1a}$;

$Q^2$ is selected from N and $CR^{1b}$, or can optionally cyclize with $Q^3$ to form a C5 or C6 saturated heterocycle;

$Q^3$ is selected from N and $CR^{1c}$, or can optionally cyclize with $Q^2$ to form a C5 or C6 saturated heterocycle;

$Q^4$ is selected from N and $CR^{1d}$; and wherein 0, 1, or 2 of $Q^1$, $Q^2$, $Q^3$, and $Q^4$ are N;

$R^{1a}$, $R^{1b}$, $R^{1c}$, and $R^{1d}$, when present, are each independently selected from hydrogen, halogen, hydroxyl, cyano, $C_1$-$C_3$ alkyl sulfone, $C_1$-$C_3$ polyhaloalkyl sulfone, $C_1$-$C_6$ alkyl, $C_1$-$C_6$ haloalkyl, $C_1$-$C_6$ polyhaloalkyl, $C_1$-$C_6$ alkoxy, ($C_1$-$C_6$)alkoxy-($C_1$-$C_6$)alkyl, ($C_1$-$C_6$)alkylamino, ($C_1$-$C_6$)haloalkyl-oxy-($C_1$-$C_6$)alkyl, ($C_1$-$C_6$)polyhaloalkyl-oxy-($C_1$-$C_6$)alkyl, ($C_1$-$C_6$)polyhaloalkyl-($C_1$-$C_6$)alkoxy, and ($C_1$-$C_6$) dialkylamino; n is 0-5;

X is independently selected from optionally substituted $CH_2$-aryl, $CH_2$-heteroaryl, $CH_2$-biaryl, or

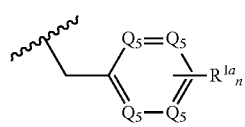

wherein:

$Q^5$ is selected from N, $CR^{1a}$, and $R^{1a}$; and n is 0-5;

$R^2$ is selected from hydrogen, $C_1$-$C_3$ alkyl, $C_1$-$C_3$ haloalkyl, and $C_1$-$C_3$ polyhaloalkyl, ($C_1$-$C_3$)polyhaloalkyl-oxy-($C_1$-$C_3$)alkyl, and ($C_1$-$C_3$)haloalkyl-oxy-($C_1$-$C_3$)alkyl, and A is optionally substituted and chosen from aryl or heteroaryl;

or a pharmaceutically acceptable salt, solvate, or polymorph thereof with a pharmaceutically acceptable carrier.

Also disclosed is a use for a compound of formula (I):

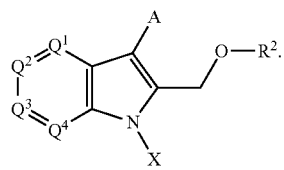

wherein:

$Q^1$ is selected from N and $CR^{1a}$;

$Q^2$ is selected from N and $CR^{1b}$, or can optionally cyclize with $Q^3$ to form a C5 or C6 saturated heterocycle;

$Q^3$ is selected from N and $CR^{1c}$, or can optionally cyclize with $Q^2$ to form a C5 or C6 saturated heterocycle;

$Q^4$ is selected from N and $CR^{1d}$; and wherein 0, 1, or 2 of $Q^1$, $Q^2$, $Q^3$, and $Q^4$ are N;

$R^{1a}$, $R^{1b}$, $R^{1c}$, and $R^{1d}$, when present, are each independently selected from hydrogen, halogen, hydroxyl, cyano, $C_1$-$C_3$ alkyl sulfone, $C_1$-$C_3$ polyhaloalkyl sulfone, $C_1$-$C_6$ alkyl, $C_1$-$C_6$ haloalkyl, $C_1$-$C_6$ polyhaloalkyl, $C_1$-$C_6$ alkoxy, ($C_1$-$C_6$)alkoxy-($C_1$-$C_6$)alkyl, ($C_1$-$C_6$)alkylamino, ($C_1$-$C_6$)haloalkyl-oxy-($C_1$-$C_6$)alkyl, ($C_1$-$C_6$)polyhaloalkyl-oxy-($C_1$-$C_6$)alkyl, ($C_1$-$C_6$)polyhaloalkyl-($C_1$-$C_6$)alkoxy, and ($C_1$-$C_6$) dialkylamino; n is 0-5;

X is independently selected from optionally substituted $CH_2$-aryl, $CH_2$-heteroaryl, $CH_2$-biaryl, or

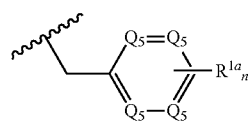

wherein:

$Q^5$ is selected from N, $CR^{1a}$, and $R^{1a}$; and n is 0-5;

$R^2$ is selected from hydrogen, $C_1$-$C_3$ alkyl, $C_1$-$C_3$ haloalkyl, and $C_1$-$C_3$ polyhaloalkyl, ($C_1$-$C_3$)polyhaloalkyl-oxy-($C_1$-$C_3$)alkyl, and ($C_1$-$C_3$)haloalkyl-oxy-($C_1$-$C_3$)alkyl, and A is optionally substituted and chosen from aryl or heteroaryl;

or a pharmaceutically acceptable salt, solvate, or polymorph thereof; in the manufacture of a medicament for use in the treatment of a thromboembolic disorder or the primary or secondary prophylaxis of a thromboembolic disorder.

Also disclosed is the use of a compound of the following formula (I):

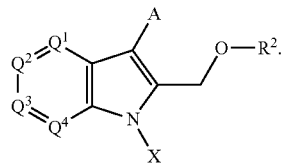

wherein:

$Q^1$ is selected from N and $CR^{1a}$;

$Q^2$ is selected from N and $CR^{1b}$, or can optionally cyclize with $Q^3$ to form a C5 or C6 saturated heterocycle;

$Q^3$ is selected from N and $CR^{1c}$, or can optionally cyclize with $Q^2$ to form a C5 or C6 saturated heterocycle;

$Q^4$ is selected from N and $CR^{1d}$; and wherein 0, 1, or 2 of $Q^1$, $Q^2$, $Q^3$, and $Q^4$ are N;

$R^{1a}$, $R^{1b}$, $R^{1c}$, and $R^{1d}$, when present, are each independently selected from hydrogen, halogen, hydroxyl, cyano, $C_1$-$C_3$ alkyl sulfone, $C_1$-$C_3$ polyhaloalkyl sulfone, $C_1$-$C_6$ alkyl, $C_1$-$C_6$ haloalkyl, $C_1$-$C_6$ polyhaloalkyl, $C_1$-$C_6$ alkoxy, ($C_1$-$C_6$)alkoxy-($C_1$-$C_6$)alkyl, ($C_1$-$C_6$)alkylamino, ($C_1$-$C_6$)haloalkyl-oxy-($C_1$-$C_6$)alkyl, ($C_1$-$C_6$)polyhaloalkyl-oxy-($C_1$-$C_6$)alkyl, ($C_1$-$C_6$)polyhaloalkyl-($C_1$-$C_6$)alkoxy, and ($C_1$-$C_6$) dialkylamino; n is 0-5;

X is independently selected from optionally substituted $CH_2$-aryl, $CH_2$-heteroaryl, $CH_2$-biaryl, or

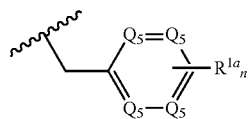

wherein:

$Q^5$ is selected from N, $CR^{1a}$, and $R^{1a}$; and n is 0-5;

$R^2$ is selected from hydrogen, $C_1$-$C_3$ alkyl, $C_1$-$C_3$ haloalkyl, and $C_1$-$C_3$ polyhaloalkyl, ($C_1$-$C_3$)polyhaloalkyl-oxy-($C_1$-$C_3$)alkyl, and ($C_1$-$C_3$)haloalkyl-oxy-($C_1$-$C_3$)alkyl, and A is optionally substituted and chosen from aryl or heteroaryl;

or a pharmaceutically acceptable salt, solvate, or polymorph thereof; in the treatment of a thromboembolic disorder or the primary or secondary prophylaxis of a thromboembolic disorder.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment of one or more thromboembolic disorder and/or any other disease state associated with PAR4 prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by a reduction of PAR4 activity" means having been subjected to a physical examination by a person of skill, for example, a physician, and found to have a condition that can be diagnosed or treated by a compound or composition that can antagonize PAR4 activity. Such a diagnosis can be in reference to a disorder, such as platelet aggregation, and the like, as discussed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "thrombotic disorders" refers to disorders characterized by formation of a thrombus that obstructs vascular blood flow. Examples of thrombotic disorders include stroke, myocardial infarction, stable or unstable angina, peripheral vascular disease, abrupt closure following angioplasty or stent placement and thrombosis induced by vascular surgery. Thrombotic disorders also include disorders characterized by formation of a thrombus caused by atrial fibrillation or inflammation.

The term "platelet aggregation" refers to the attachment of activated platelets one to another, which results in the formation of aggregates or clumps of activated platelets.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents. Unless otherwise specified, the substituents are all independent from one another.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, thioether, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1-OA^2$ or $—OA^1-(OA^2)_a-OA^3$, where "a" is an integer of from 1 to 200 and $A^1$, $A^2$, and $A^3$ are alkyl and/or cycloalkyl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus.

Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "heterocycle," as used herein refers to single and multi-cyclic aromatic or non-aromatic ring systems in which at least one of the ring members is other than carbon. Heterocycle includes pyridinde, pyrimidine, pyrazine, furan, thiophene, pyrrole, isoxazole, isothiazole, pyrazole, oxazole, thiazole, imidazole, oxazole, oxadiazole including, for example, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, imidazothiadiazole, imidazooxadiazole, imidazothiazole, thiazolotriazole, and the like.

The term "hydroxyl" as used herein is represented by a formula —OH.

The term "thiol" as used herein is represented by a formula —SH.

The term "thioester" as used herein is represented by a formula $—S—CH_3$.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

In some aspects, a structure of a compound can be represented by a formula:

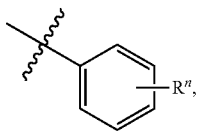

which is understood to be equivalent to a formula:

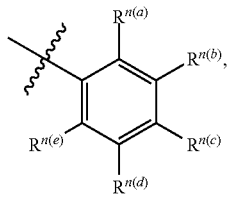

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. Likewise, when a group R is defined as four substituents, R is understood to represent four independent substituents, $R^a$, $R^b$, $R^c$, and $R^d$. Unless indicated to the contrary, the substituents are not limited to any particular order or arrangement.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds, or pharmaceutically acceptable derivatives thereof, useful as antagonists of PAR4. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In one aspect, the invention relates to compounds having a structure represented by formula (I):

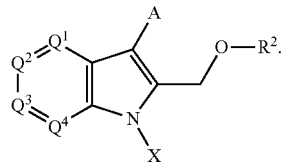

wherein:
$Q^1$ is selected from N and $CR^{1a}$;
$Q^2$ is selected from N and $CR^{1b}$, or can optionally cyclize with $Q^3$ to form a C5 or C6 saturated heterocycle;
$Q^3$ is selected from N and $CR^{1c}$, or can optionally cyclize with $Q^2$ to form a C5 or C6 saturated heterocycle;
$Q^4$ is selected from N and $CR^{1d}$; and wherein 0, 1, or 2 of $Q^1$, $Q^2$, $Q^3$, and $Q^4$ are N;
$R^{1a}$, $R^{1b}$, $R^{1c}$ and $R^{1d}$, when present, are each independently selected from hydrogen, halogen, hydroxyl, cyano, $C_1$-$C_3$ alkyl sulfone, $C_1$-$C_3$ polyhaloalkyl sulfone, $C_1$-$C_6$ alkyl, $C_1$-$C_6$ haloalkyl, $C_1$-$C_6$ polyhaloalkyl, $C_1$-$C_6$ alkoxy, ($C_1$-$C_6$)alkoxy-($C_1$-$C_6$)alkyl, ($C_1$-$C_6$)alkylamino, ($C_1$-$C_6$)haloalkyl-oxy-($C_1$-$C_6$)alkyl, ($C_1$-$C_6$)polyhaloalkyl-oxy-($C_1$-$C_6$)alkyl, ($C_1$-$C_6$)polyhaloalkyl-($C_1$-$C_6$)alkoxy, and ($C_1$-$C_6$)dialkylamino; n is 0-5;
X is independently selected from optionally substituted $CH_2$-aryl, $CH_2$-heteroaryl, $CH_2$-biaryl, or

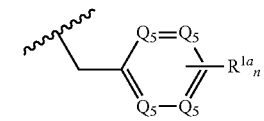

wherein:
$Q^5$ is selected from N, $CR^{1a}$, and $R^{1a}$; and
n is 0-5;
$R^2$ is selected from hydrogen, $C_1$-$C_3$ alkyl, $C_1$-$C_3$ haloalkyl, and $C_1$-$C_3$ polyhaloalkyl, ($C_1$-$C_3$)polyhaloalkyl-oxy-($C_1$-$C_3$)alkyl, and ($C_1$-$C_3$)haloalkyl-oxy-($C_1$-$C_3$)alkyl, and
A is optionally substituted and chosen from aryl or heteroaryl;
or a pharmaceutically acceptable salt, solvate, or polymorph thereof.

Also disclosed are compounds wherein A is selected from imidazolyl, oxadiazolyl, oxazolyl, pyrazinyl, pyrazolyl, pyridinyl, pyrimidinyl, thiadiazolyl, thiazolyl, imidazothiadiazolyl, imidazooxadiazole, imidazothiazole, thiazolotriazole, and triazolyl.

Also disclosed are compounds of the following formula:

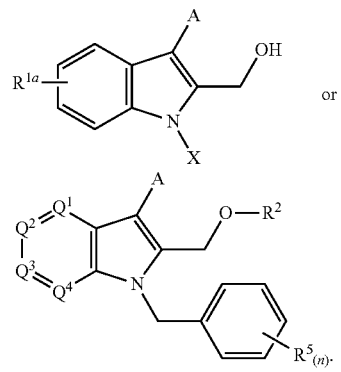

Also disclosed are compounds of formula (I), wherein A is substituted or unsubstituted pyridinyl. In another embodiment, A is substituted or unsubstituted 2-pyridinyl. In another embodiment, A is alkoxy substituted.

Also disclosed are compounds of formula (I), wherein $R^1$ is hydrogen, halogen, cyano, —O—$CF_3$, alkoxy, or $CF_3$.

Also disclosed are compounds of formula (I), wherein $Q^2$ and $Q^3$ together form dioxolane.

Also disclosed are compounds of formula (I), wherein $Q^2$ is substituted with —O—$CF_3$.

Also disclosed are compounds where at least one of $Q^2$-$Q^4$ is substituted with cyano, $C_1$-$C_3$ thioester, or —O—$CF_3$.

Also disclosed are compounds of formula (I), wherein each $Q^5$ is $CR^{1a}$.

Also disclosed are the following compounds:

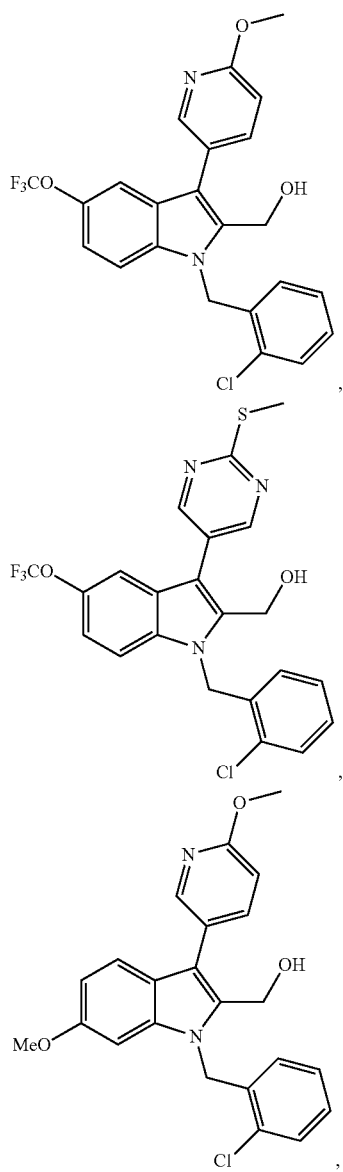

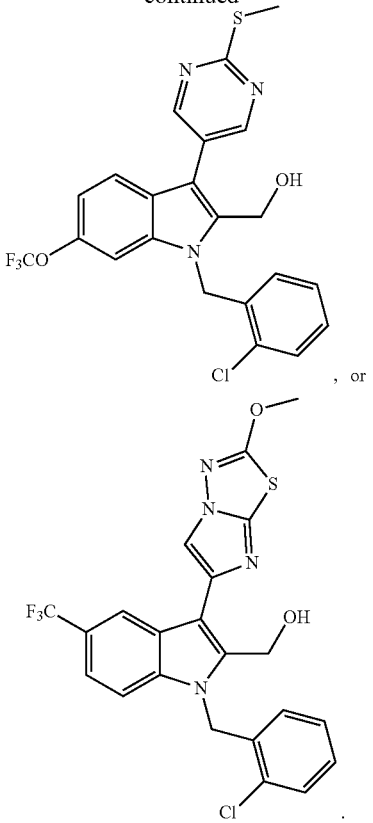

Also disclosed are the following compounds:

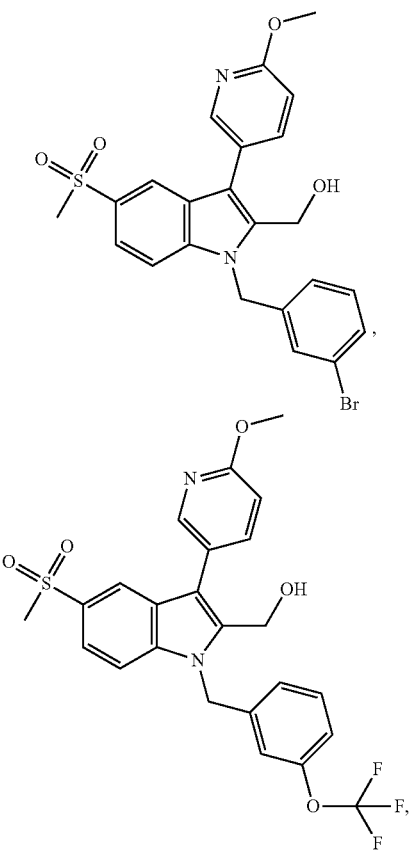

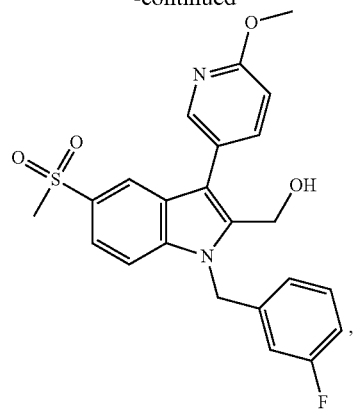
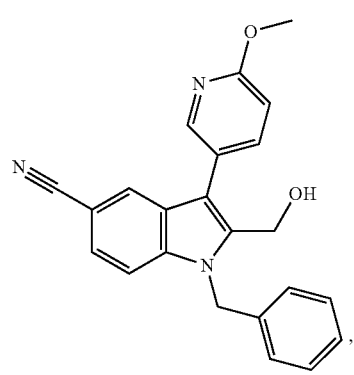
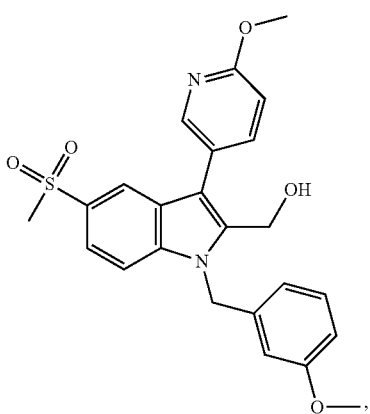
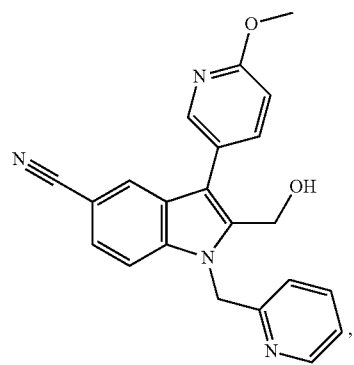
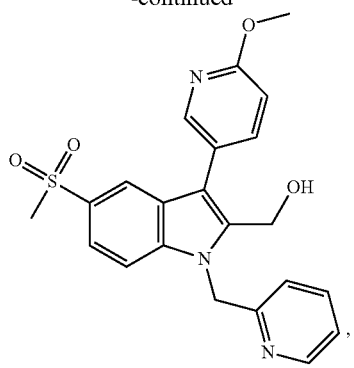
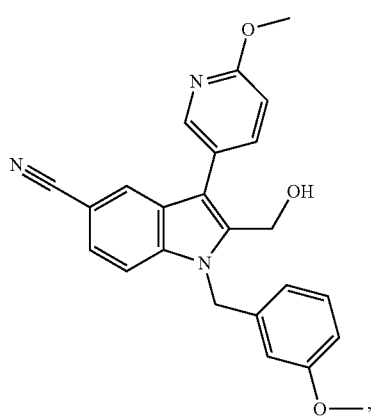
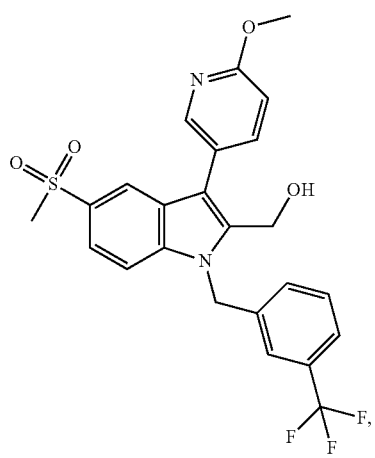
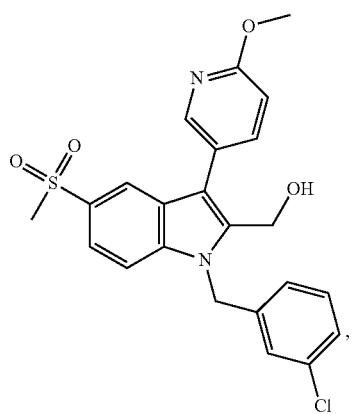

-continued
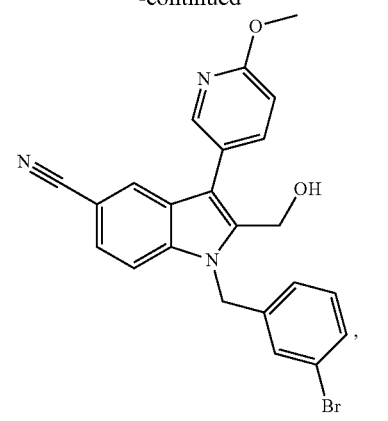
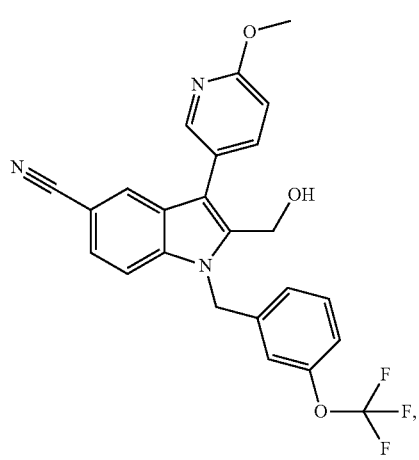
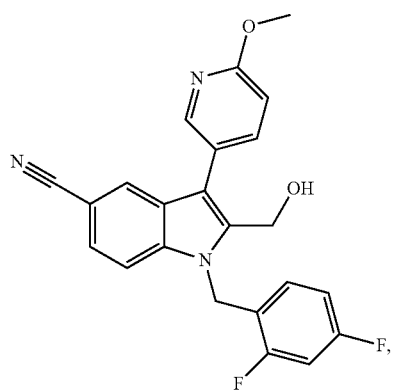
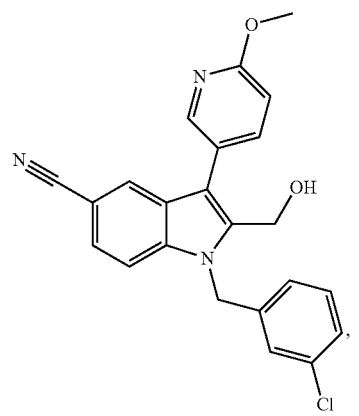
-continued
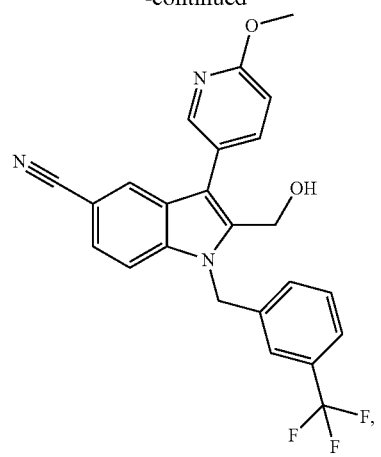
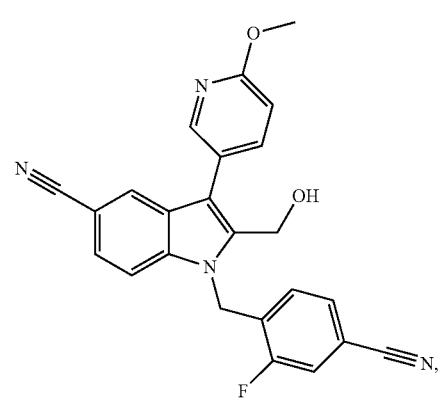
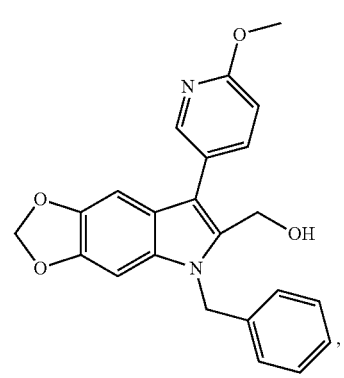
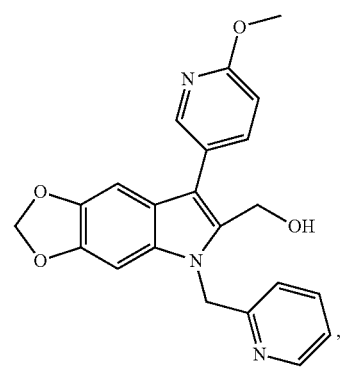

-continued
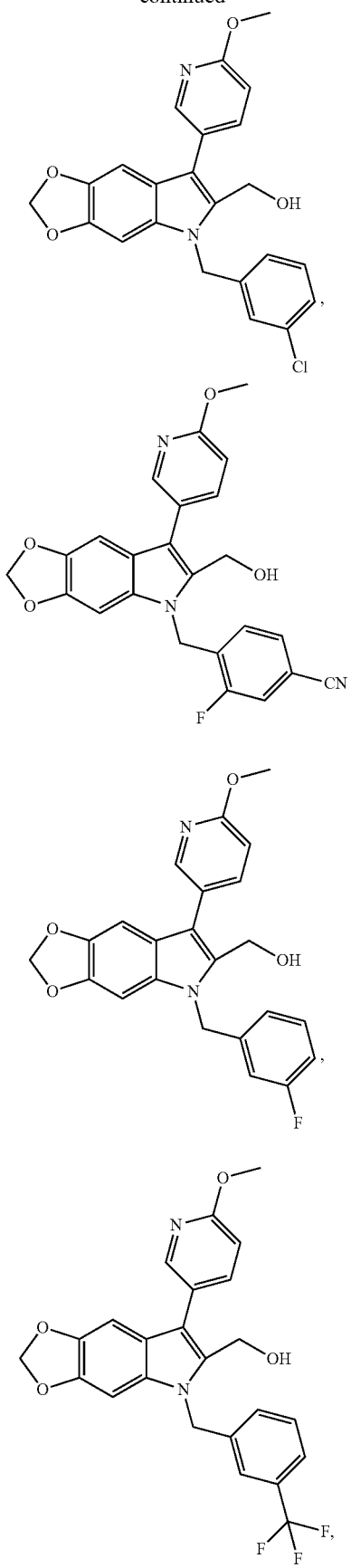
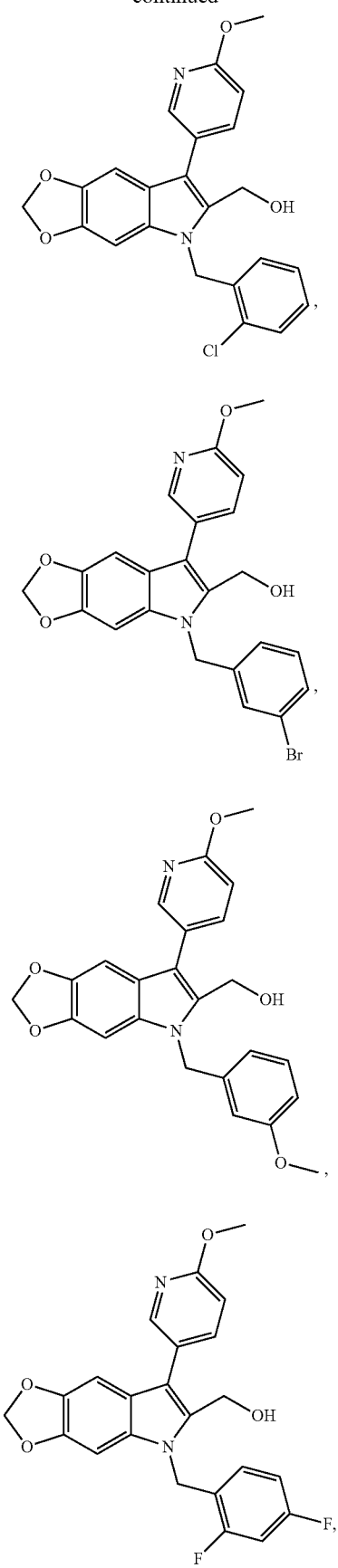

25
-continued
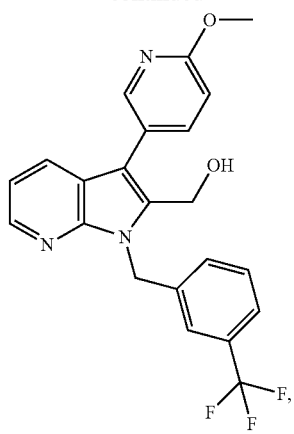
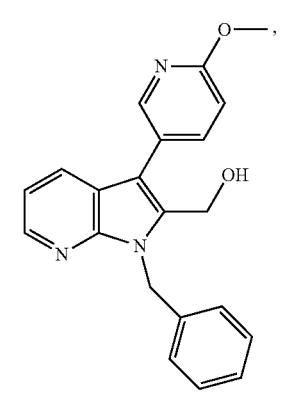
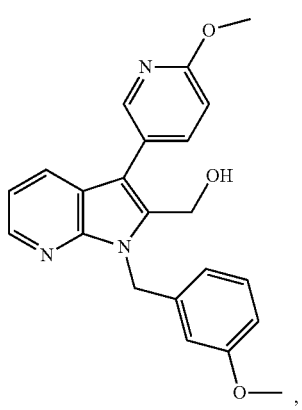
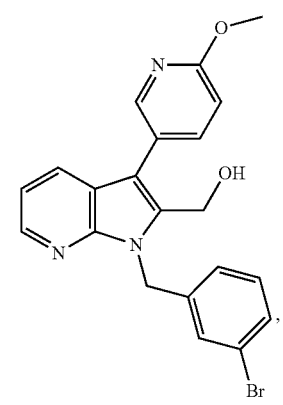
26
-continued
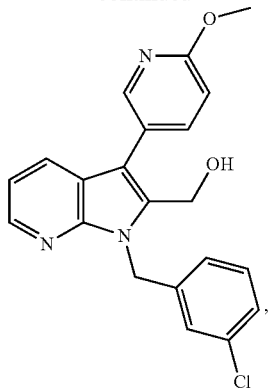
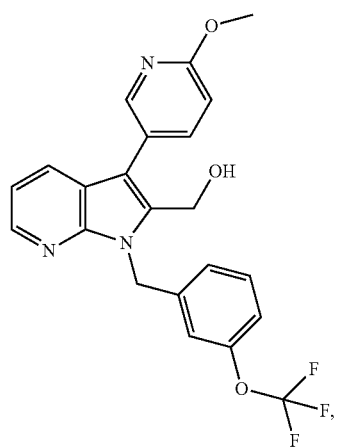
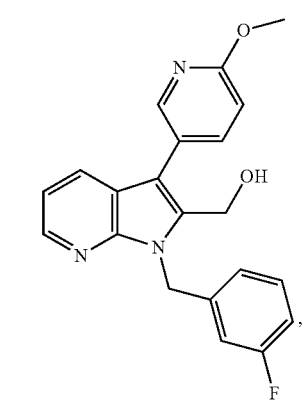
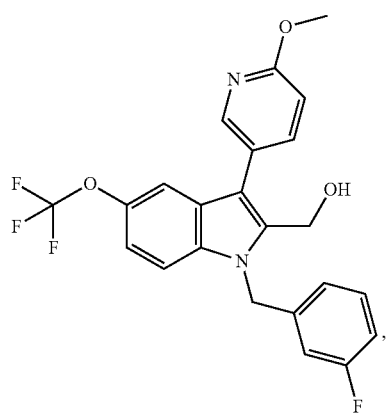

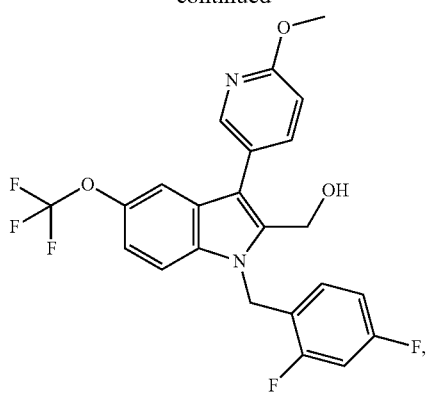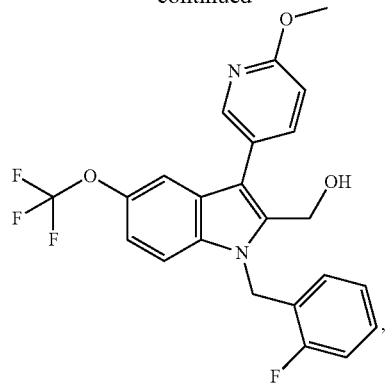

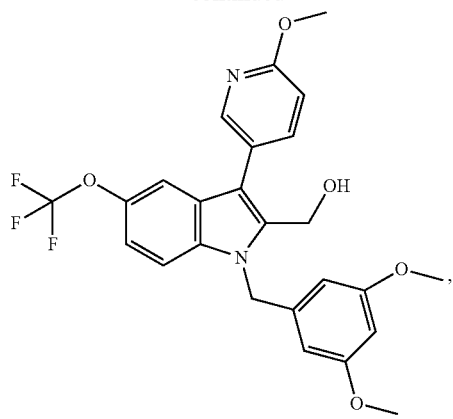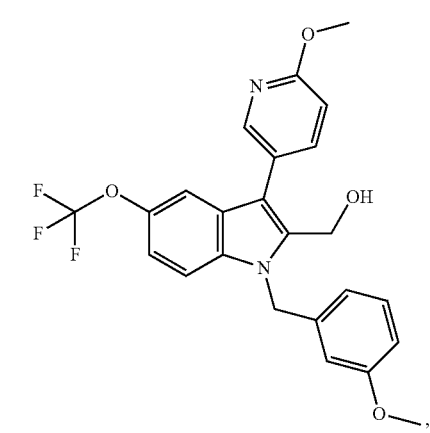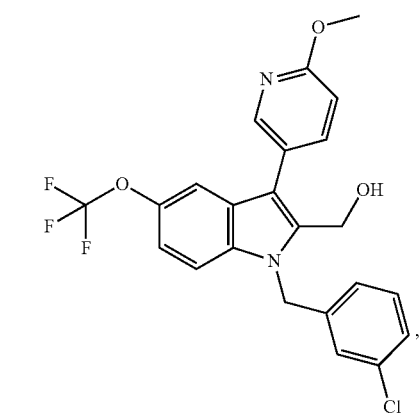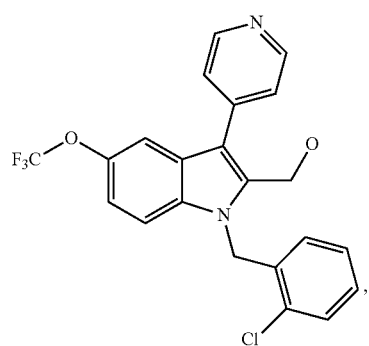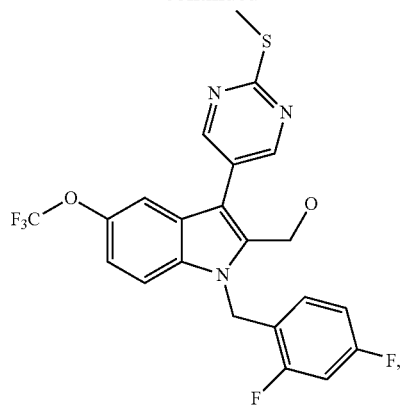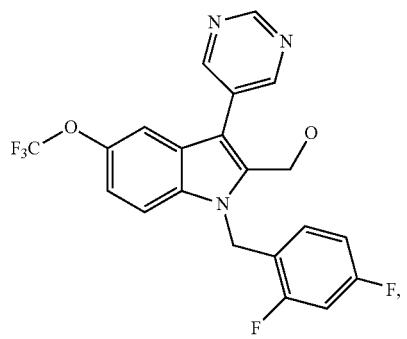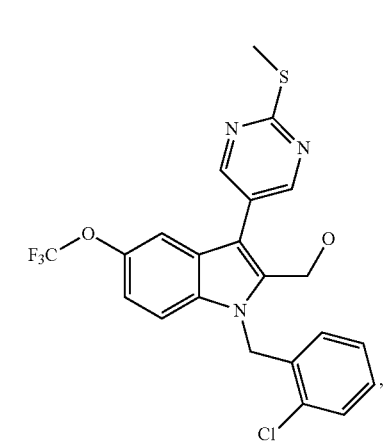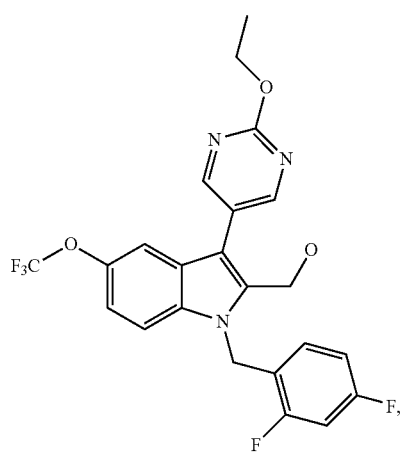

31
-continued
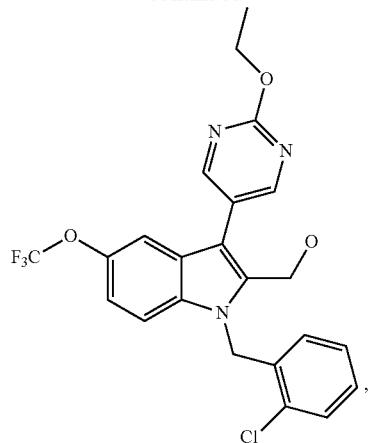
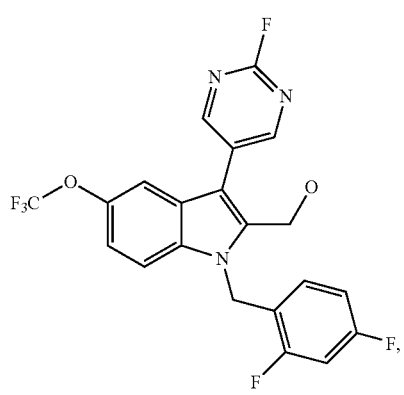
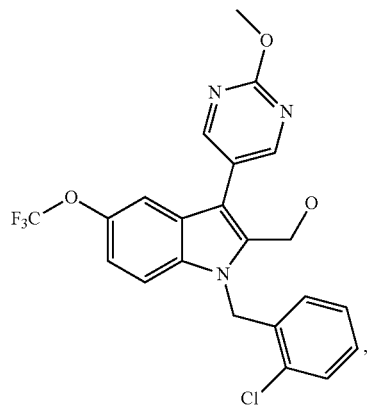
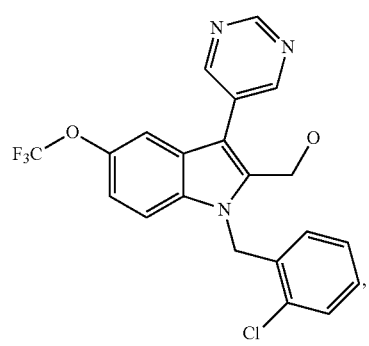
32
-continued
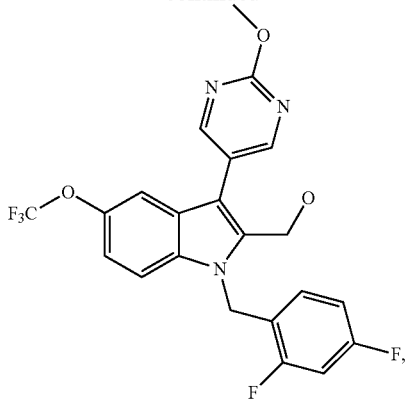
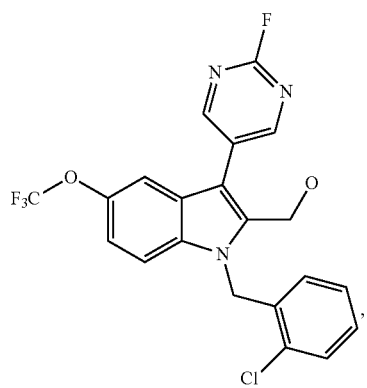
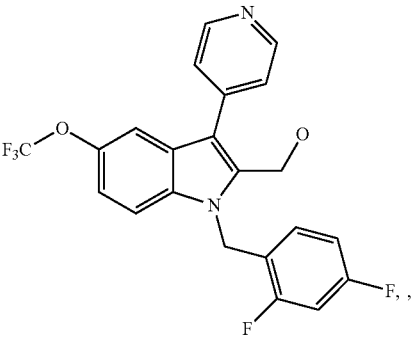
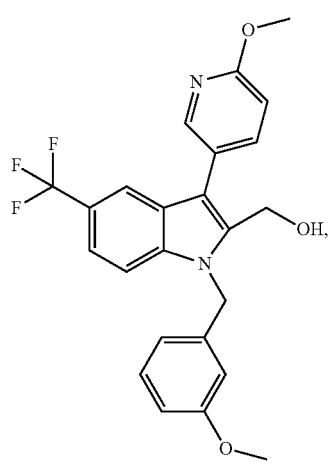

-continued
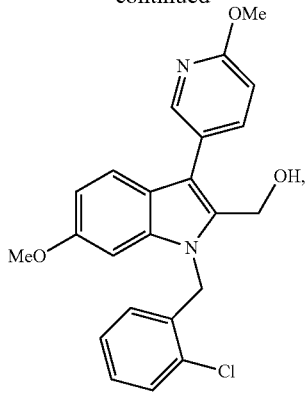
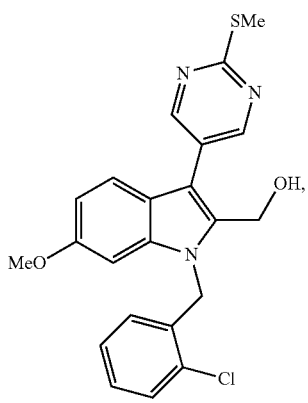
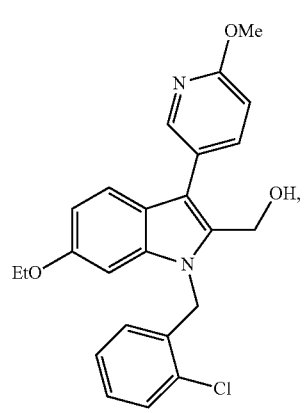
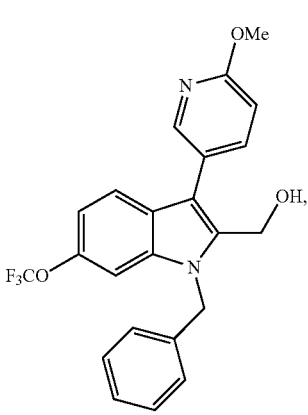
-continued
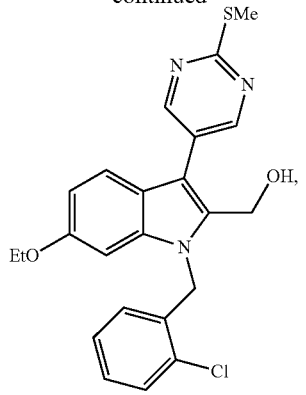
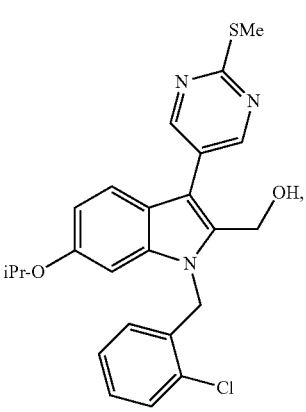
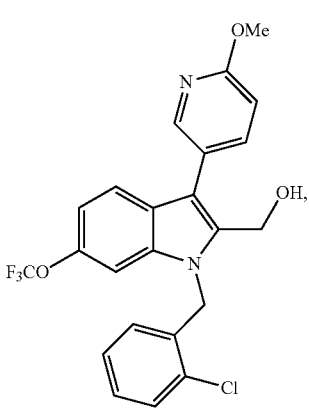
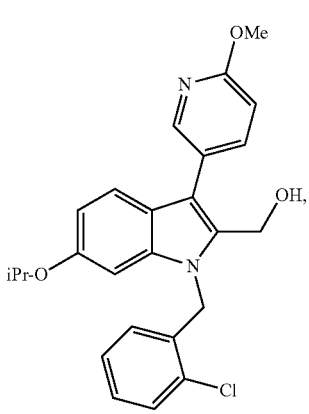

35
-continued
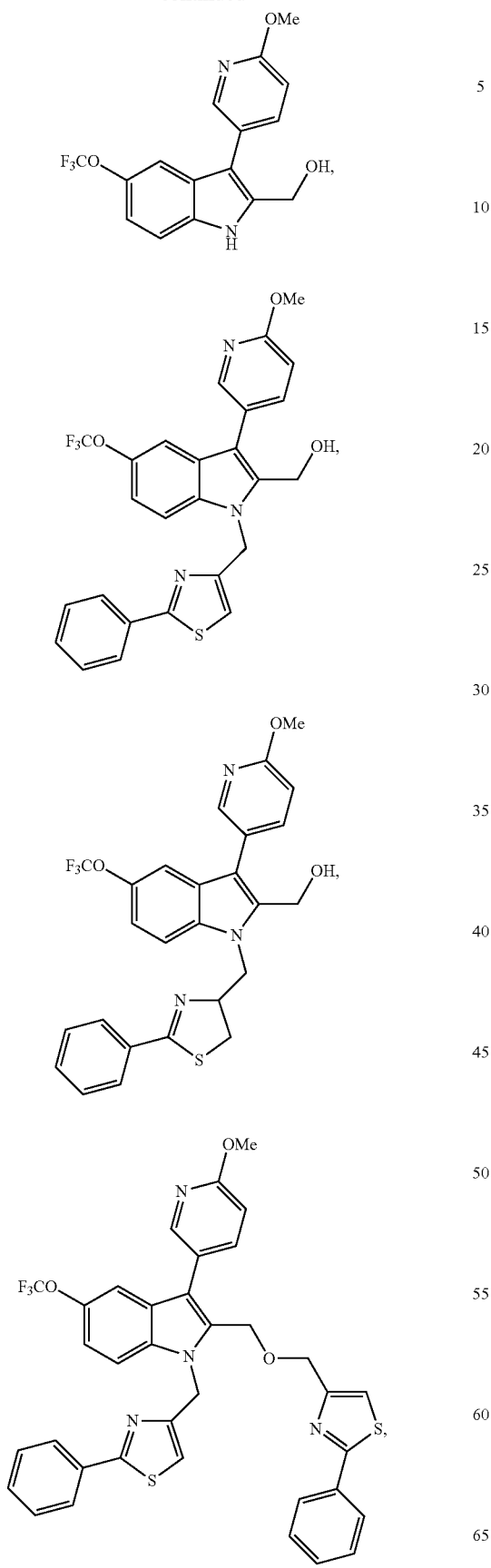
36
-continued
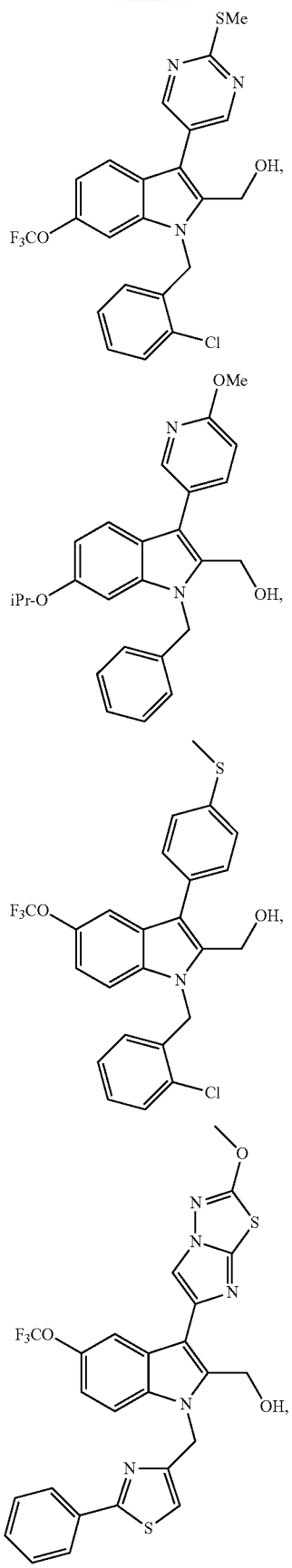

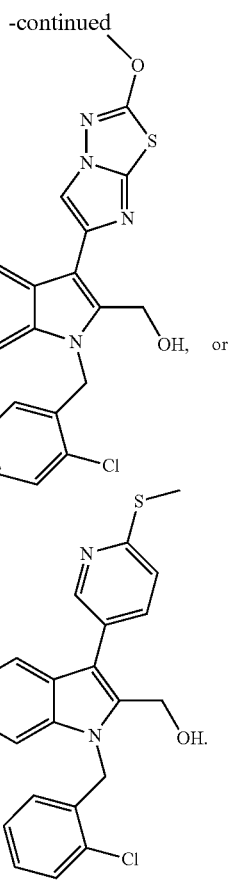

The compounds disclosed herein can include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

The analogs (compounds) of the present disclosure are arranged into several categories to assist the formulator in applying a rational synthetic strategy for the preparation of analogs which are not expressly exampled herein. The arrangement into categories does not imply increased or decreased efficacy for any of the compositions of matter described herein.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer of a compound may be obtained by stereoselective synthesis using optically pure starting materials or reagents of known configuration by methods well known in the art.

C. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed PAR4 antagonists and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be coadministered, either in concomitant therapy or in a fixed combination.

In one aspect, the compound can be employed in combination with at least one additional therapeutic agent. In one aspect of the invention the at least one additional therapeutic agent may be an anti-platelet agent. In one aspect, the anti-platelet agent(s) are P2Y12 antagonists and/or aspirin. The P2Y12 antagonists may be clopidogrel, ticagrelor, or prasugrel. In another aspect of the invention, the at least one additional therapeutic agent(s) may be an anticoagulant. The anticoagulant agent(s) may be FXa inhibitors or thrombin inhibitors. For example, the FXa inhibitors are apixaban or rivaroxaban. Additionally, the thrombin inhibitor may be dabigatran.

In one aspect, the invention relates to pharmaceutical compositions comprising a compound having a structure represented by a formula (I):

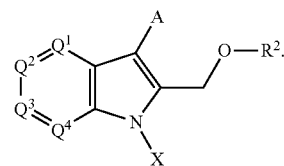

wherein:

$Q^1$ is selected from N and $CR^{1a}$;

$Q^2$ is selected from N and $CR^{1b}$, or can optionally cyclize with $Q^3$ to form a C5 or C6 saturated heterocycle;

$Q^3$ is selected from N and $CR^{1c}$, or can optionally cyclize with $Q^2$ to form a C5 or C6 saturated heterocycle;

$Q^4$ is selected from N and $CR^{1d}$; and wherein 0, 1, or 2 of $Q^1$, $Q^2$, $Q^3$, and $Q^4$ are N;

$R^{1a}$, $R^{1b}$, $R^{1c}$, and $R^{1d}$, when present, are each independently selected from hydrogen, halogen, hydroxyl, cyano, $C_1$-$C_3$ alkyl sulfone, $C_1$-$C_3$ polyhaloalkyl sulfone, $C_1$-$C_6$ alkyl, $C_1$-$C_6$ haloalkyl, $C_1$-$C_6$ polyhaloalkyl, $C_1$-$C_6$ alkoxy, $(C_1$-$C_6)$alkoxy-$(C_1$-$C_6)$alkyl, $(C_1$-$C_6)$alkylamino, $(C_1$-$C_6)$ haloalkyl-oxy-$(C_1$-$C_6)$alkyl, $(C_1$-$C_6)$polyhaloalkyl-oxy-$(C_1$-$C_6)$alkyl, $(C_1$-$C_6)$polyhaloalkyl-$(C_1$-$C_6)$alkoxy, and $(C_1$-$C_6)$ dialkylamino; n is 0-5;

X is independently selected from optionally substituted $CH_2$-aryl, $CH_2$-heteroaryl, $CH_2$-biaryl, or

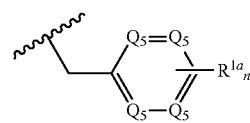

wherein:

$Q^5$ is selected from N, $CR^{1a}$, and $R^{1a}$; and n is 0-5;

$R^2$ is selected from hydrogen, $C_1$-$C_3$ alkyl, $C_1$-$C_3$ haloalkyl, and $C_1$-$C_3$ polyhaloalkyl, $(C_1$-$C_3)$polyhaloalkyl-oxy-$(C_1$-$C_3)$alkyl, and $(C_1$-$C_3)$haloalkyl-oxy-$(C_1$-$C_3)$alkyl, and A is optionally substituted and chosen from aryl or heteroaryl;

or a pharmaceutically acceptable salt, solvate, or polymorph thereof, and a pharmaceutically acceptable carrier.

D. Uses

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I or stereoisomers, tautomers, pharmaceutically acceptable salts, prodrug esters, or solvates thereof.

The thromboembolic disorder may be selected from the group consisting of acute coronary syndrome, unstable angina, stable angina, ST-elevated myocardial infarction, non-ST-elevated myocardial infarction, atrial fibrillation, myocardial infarction, transient ischemic attack, stroke, atherosclerosis, peripheral arterial disease, venous thrombosis, deep vein thrombosis, thrombophlebitis, arterial embolism, coronary arterial thrombosis, cerebrovascular injury, cerebral arterial thrombosis, cerebral embolism, kidney embolism, pulmonary embolism, cancer-related thrombosis, and thrombosis resulting from medical implants, devices, and procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of a PAR4 antagonist, which is a compound of Formula I.

In some embodiments, the invention provides a method of treatment or prophylaxis of a thromboembolic disorder involving administering to a subject in need thereof (e.g., a human) a therapeutically effective amount of a compound that binds to PAR4 (such as a compound of Formula I of the invention) and inhibits PAR4 cleavage and/or signaling, wherein said subject has a dual PAR1/PAR4 platelet receptor repertoire.

In some embodiments, the present invention provides a compound of the present invention or stereoisomers, tautomers, pharmaceutically acceptable salts, solvates, or prodrug esters thereof, for use in therapy for the treatment or prophylaxis of a thromboembolic disorder.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of a thromboembolic disorder.

In some embodiments, compounds of the present invention may be co-administered with at least one additional drug or therapeutic agent. In certain embodiments of the preset invention, the at least one additional therapeutic agent(s) are an anti-platelet agent or a combination thereof. Examples of the anti-platelet agents include P2Y12 antagonists and/or aspirin. Preferably, the P2Y12 antagonists are clopidogrel, ticagrelor, or prasugrel. In another embodiment, the at least one additional therapeutic agent is an anticoagulant. Examples of the anticoagulant agent include FXa inhibitors or thrombin inhibitors. The FXa inhibitors may be, for example, apixaban or rivaroxaban. The thrombin inhibitor may be, for example, dabigatran.

Further examples include therapeutics such as a thrombolytic, anticoagulant or antiplatelet agent. Typically, the antithrombotic is aspirin, heparin, heparin sulfate, danaparoid sodium, clopidogrel, prasugrel, ticagrelor, cangrelor, elinogrel, cilostazol, abciximab, eptifibatide, tirofiban, dipyridamole, epoprostenol, abciximab, eptifibatide, tirofiban, beraprost, prostacyclin, iloprost, and treprostinil, aloxiprin, carbasalate calcium, indobufen, triflusal dipyridamole, picotamide, terutroban, triflusal cloricromen, ditazole, acenocoumarol, coumatetralyl, dicoumarol, ethyl biscoumacetate, phenprocoumon, warfarin, clorindione, diphenadione, phenindione, tioclomarol, defibrotide, ramatroban, antithrombin III, and/or protein C (drotrecogin alfa) or combinations thereof.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

E. Examples/Experimental

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer of a compound may be obtained by stereoselective synthesis using optically pure starting materials or reagents of known configuration by methods well known in the art.

1. Preparation of Exemplary Compounds

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Example compounds of type 1.5 can be prepared according to Scheme 1 starting from an appropriate indole ester 1.1, bromination furnishes ester 1.2. Suzuki cross-coupling provides 1.3 followed by alkylation using 1.6 gives ester 1.4. Final reduction using LiBH4 or a related aluminium or boron reducing agent provides examples 1.5.

Alternatively, novel indole ring systems 2.2 can be obtained using various 1,5-aryl and heteroaryl bromocarboxaldehydes of type 2.1 and ethyl isocyanoacetate in a highly efficient one-pot copper (I) catalyzed condensation/coupling/deformylation process to afford key intermediate indoles of type 2.2 in good yield (Cai, Q.; Li, Z.; Wei, J.; Ha, C.; Pei, C.; Ding, K. *Chem. Commun.* 2009, 7581-7583.) Subsequent bromination, Suzuki cross-coupling, alkylation, and ester reduction provides examples of type 2.5.

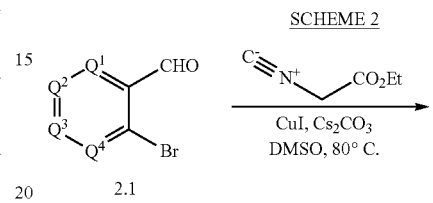

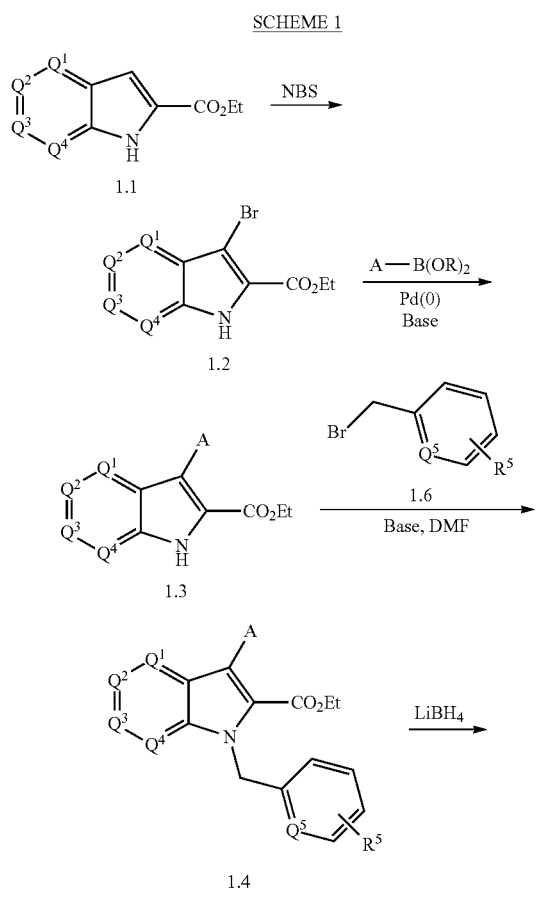

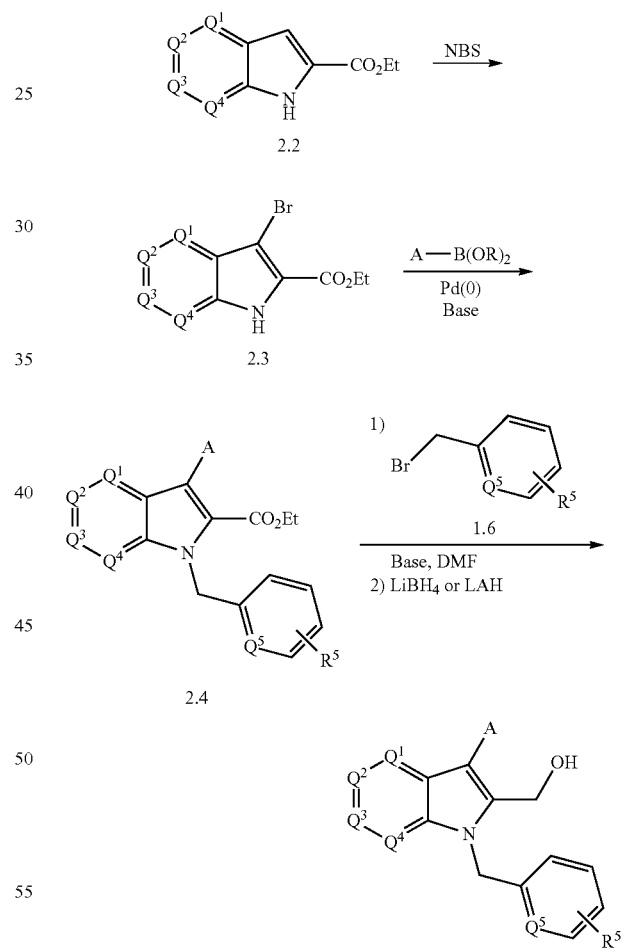

Intermediate benzyl alkylating agents of type 1.6 as described above are either commercially available or can be prepared according to Scheme 3. Beginning with acid or ester 3.1, reduction affords 3.2 which can be transformed to mesylate 3.3, bromide 1.6, or chloride 3.4 using known methods and used throughout to prepare final examples.

SCHEME 3

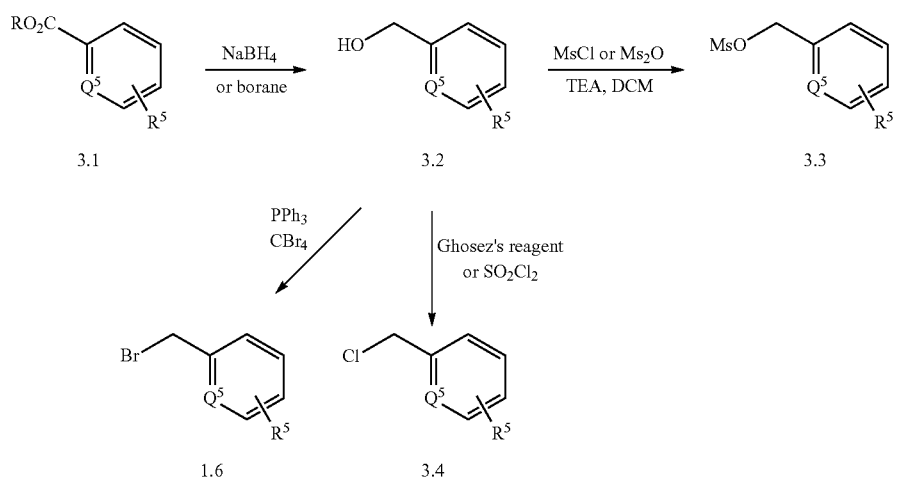

In addition, example compounds of type 4.2 can be prepared according to Scheme 4 starting from prior alcohol examples 4.1, as previously described. Alkylation using a functionalized alkyl halide reagent $R_2X$ in the presence of a base, such as sodium hydride, in an aprotic polar solvent, such as DMF, gives ethers of type 4.2.

SCHEME 4

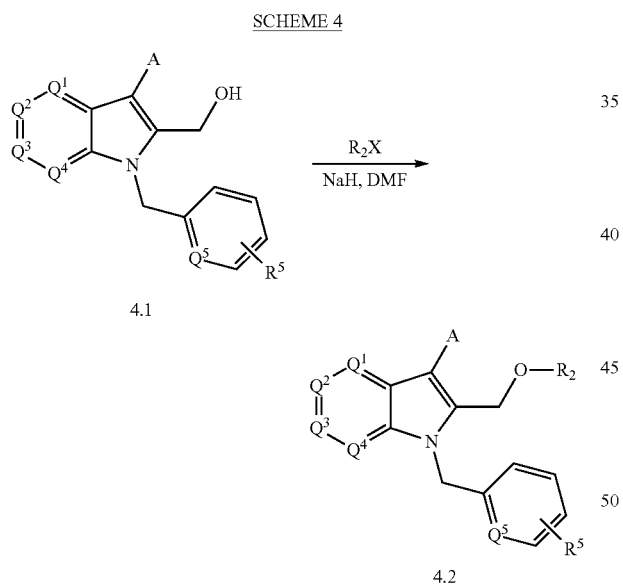

The preparation of analogs bearing A groups with 5,5-bicycylic heterocycles, such as 2-methoxy-6-imidazo[2,1-b][1,3,4]thiadiazoles, can be prepared according to Scheme 5 starting from the desired 2-carboxy indole obtained from commercial sources, Scheme 2, or other indole methodologies familiar to those skilled in the art. Thus starting from indole 5.1, acylation using a Lewis acid, such as tin (IV) chloride, and acetic anhydride affords 5.2. Selective alpha-chlorination with benzyltrimethylammonium dichloroiodate (Kajigaeshi, S., et al., Synthesis Communications, 1988, 545.) affords intermediate chloro ketone 5.3. Displacement with sodium bromide followed by condensation with an aminothiadiazole affords intermediate 5.4. Displacement with alkoxide, followed by alkylation and reduction gives final examples of type 5.7.

SCHEME 5

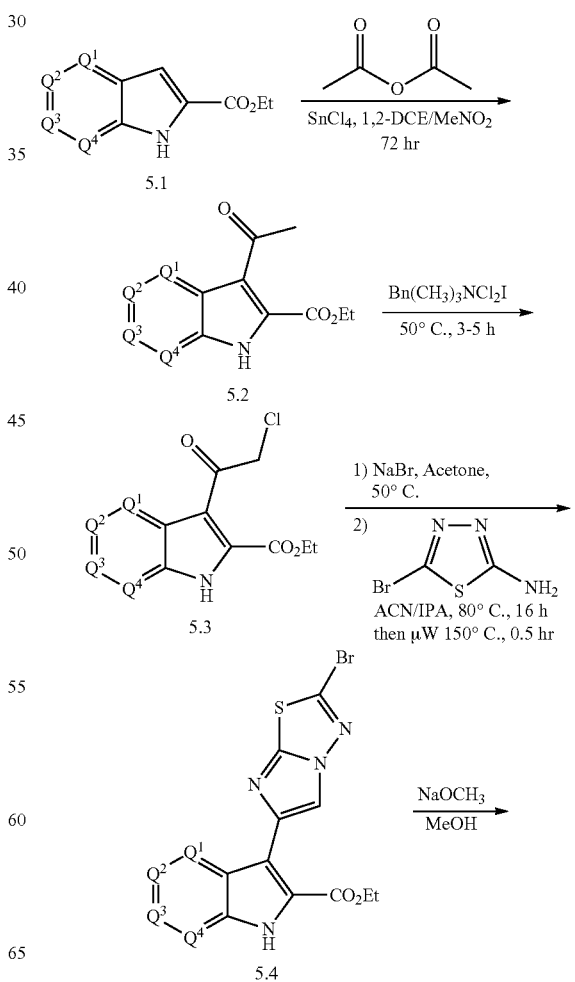

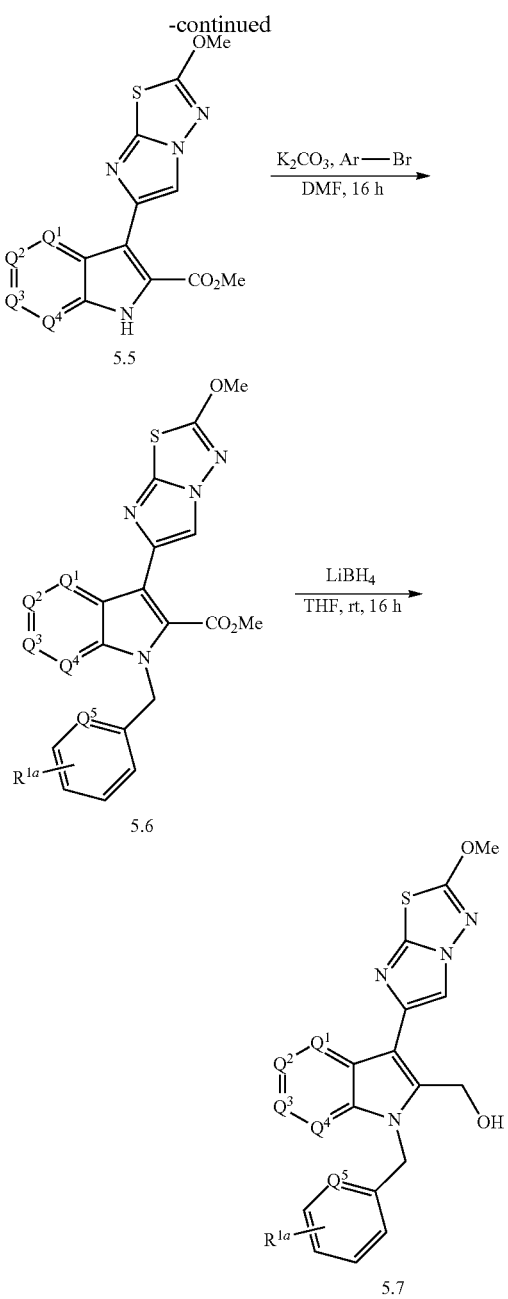

2. Experimental

Hereinafter, the term "EtOAc" means ethyl acetate, "DCM" means dichloromethane, "DIPEA" means N,N-diisopropylethylamine, "DMF" means N,N-dimethylformamide, "THF" means tetrahydrofuran, "DTBAD" means di-tert-butyl azodicarboxylate, "HATU" means 2-(7-aza-1H-benzotriazole-1-yl)-1,1,3,3-tetramethyluronium hexafluorophosphate, "LCMS" means liquid chromatography/mass spectrometry, "MeOH" means methanol, "[M+H]$^+$" means the protonated mass of the free base of the compound, "M. p." means melting point, "NMR" means nuclear magnetic resonance, "$R_t$" means retention time (in minutes), "THF" means tetrahydrofuran, "rt" means room temperature.

Microwave assisted reactions were performed in a single-mode reactor: Emrys™ Optimizer microwave reactor (Personal Chemistry A.B., currently Biotage).

Hydrogenation reactions were performed in a continuous flow hydrogenator H-CUBE® from ThalesNano Nanotechnology Inc. or using a Parr hydrogenation shaker apparatus.

Analytical thin layer chromatography was performed on Analtech silica gel GF 250 micron plates using reagent grade solvents. Normal phase flash silica gel-based column chromatography was performed using ready-to-connect cartridges from ISCO, on irregular silica gel, particle size 15-40 μm on a Combi-flash Companion chromatography system from ISCO.

Low resolution mass spectra were obtained on an Agilent 1200 series 6130 mass spectrometer. High resolution mass spectra were recorded on a Waters Q-TOF API-US. Analytical HPLC was performed on an HP 1100 with UV detection at 214 and 254 nm along with ELSD detection, LC/MS (J-Sphere80-C18, 3.0×50 mm, 4.1 min gradient, 5% [0.05% TFA/CH$_3$CN]:95% [0.05% TFA/H$_2$O] to 100% [0.05% TFA/CH$_3$CN]. Preparative RP-HPLC purification was performed on a custom HP 1100 automated purification system with collection triggered by mass detection or using a Gilson Inc. preparative UV-based system using a Phenomenex Luna C18 column (50×30 mm I.D., 5 μm) with an acetonitrile (unmodified)-water (0.1% TFA) custom gradient.

For LC-MS-characterization of the compounds of the present invention, the following methods were used:

Method 1: The HPLC measurement was performed using an Agilent 1200 system comprising a binary pump with degasser, an autosampler, a column oven, a diode-array detector (DAD) and a column as specified in the respective methods below. Flow from the column was split to a SQ mass spectrometer and Polymer Labs ELSD. The MS detector was configured with an ES ionization source. Nitrogen was used as the nebulizer gas. The source temperature was maintained at 350° C. Data acquisition was performed with Agilent Chemstation software. Reversed phase HPLC was carried out on a Kinetex C18 column (2.6 μm, 2.1×30 μm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 μL. Low-resolution mass spectra (single quadruple MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V. Method 2: Using method 1 instrument and column conditions. The gradient conditions used are: 93% A (water+0.1% TFA), 7% B (acetonitrile), to 95% B in 2.0 minutes, returning to initial conditions at 2.11 minutes. Injection volume 1 μL. Low-resolution mass spectra (single quadruple MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V.

Chiral purification of racemic mixtures was readily accomplished using a supercritical fluid chromatography (SFC) instrument from Thar Scientific Instruments. Chiral analytical and semi-prep SFC purification columns were from Chiral Technologies.

$^1$H and $^{13}$C NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

a. Preparation of Intermediates

Intermediate A1. Ethyl 3-bromo-5-(trifluoromethoxy)-1H-indole-2-carboxylate

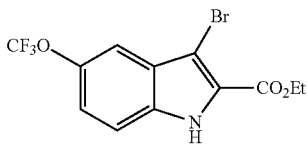

To a THF solution (3 mL) of commercially available ethyl 5-(trifluoromethoxy)-1H-indole-2-carboxylate (300 mg, 1.098 mmol, 1 eq.) was added dropwise the THF (5 mL) solution of N-bromosuccinimide (214.7 mg, 1.206 mmol, 1.1 eq.). The mixture was stirred at rt for 2 h. THF was removed under reduced pressure to afford crude ethyl 3-bromo-5-(trifluoromethoxy)-1H-indole-2-carboxylate. The product was purified via automated flash chromatography (0-10% EtOAc/hexanes, 382 mg, 99%): LC-MS, >98% (215, 254 nm), Rt=1.276, m/z=351.8 [M+H]; $^1$H NMR(400 MHz, CDCl$_3$) 1.46 (t, J=7.1, 3H), 4.44-4.50 (q, J=7.1, 2H), 7.23 (d, J=1.4, 1H), 7.38-7.42 (dd, J=4.7, 8.9, 1H), 7.53 (d, J=16.1, 1H), 9.12 (s, 1H).

Intermediate A2. Ethyl 3-bromo-5-(trifluoromethyl)-1H-indole-2-carboxylate

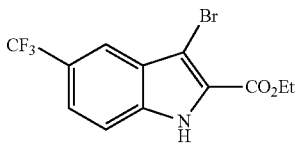 [SMILES: CCOC(=O)c1[nH]c2ccc(C(F)(F)F)cc2c1Br]

Step 1

To a dry and argon-filled vial was added 2-bromo-5-(trifluoromethyl)benzaldehyde (500 mg, 1.82 mmol), ethyl 2-isocyanoacetate (226 mg, 230 μL, 2.00 mmol), CsCO$_3$ (1186 mg, 3.64 mmol), CuI (35 mg, 0.182 mmol) and DMSO (10 mL). The mixture was allowed to stir overnight at 50° C. Upon completion, the solution was passed through Celite and was concentrated under reduced pressure. The crude product was purified by RP-HPLC to afford ethyl 5-(trifluoromethyl)-1H-indole-2-carboxylate (332 mg, 71%): LC-MS, >98% (215, 254 nm), Rt=1.157, m/z=257.9 [M+H]; $^1$H NMR (400 MHz, CDCl$_3$) 1.44 (t, J=7.1, 3H), 4.42-4.47 (q, J=7.1, 2H), 7.29-7.30 (dd, J=0.5, 1.9, 1H), 7.50-7.55 (m, 2H), 8.00 (d, J=0.7, 1H), 9.28 (s, 1H); $^{13}$C NMR (100 MHz, CDCl$_3$) 14.5, 61.6, 109.3, 112.5, 120.6 (q, J=4.3), 121.9 (q, J=3.2), 123.5 (q, J=31.8), 125.0 (q, J=271.6), 126.8, 129.4, 138.0, 161.8.

Step 2

To a THF solution (3 mL) of ethyl 5-(trifluoromethyl)-1H-indole-2-carboxylate (310 mg, 1.205 mmol) was added dropwise a THF (5 mL) solution of N-bromosuccinimide (321 mg, 1.807 mmol). The mixture was stirred at rt for 2 h. THF was removed under reduced pressure to afford the crude ethyl 3-bromo-5-(trifluoromethyl)-1H-indole-2-carboxylate. Purification using automated flash chromatography (SiO$_2$ 0-10% EtOAc/hexanes) afforded title product (401 mg, 99%): LC-MS, >98% (215, 254 nm), Rt=1.248, m/z=373.0 [M+2H$_2$O+H], 335.7 [M+H]; $^1$H NMR (400 MHz, DMSO-d$_6$) 1.37 (d, J=7.1, 3H), 4.36-4.42 (q, J=7.1, 2H), 7.60-7.62 (dd, J=1.6, 8.8, 1H), 7.67 (d, J=8.7, 1H), 7.83 (s, 1H).

b. Preparation of Representative Compounds

Example 1

(Table 1, B13) (1-(3-methoxybenzyl)-3-(6-methoxypyridin-3-yl)-5-(trifluoromethyl)-1H-indol-2-yl)methanol

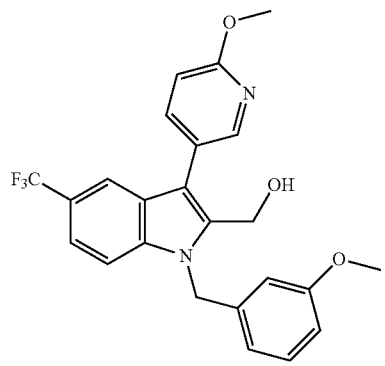 [SMILES: COc1cccc(Cn2c(CO)c(-c3ccc(OC)nc3)c3cc(C(F)(F)F)ccc32)c1]

Step 1

To a microwave vial was added ethyl 3-bromo-5-(trifluoromethyl)-1H-indole-2-carboxylate (Intermediate A2) (100 mg, 0.30 mmol), 6-methoxy-3-pyridinyl-boronic acid (70.8 mg, 0.48 mmol), Pd(PPh$_3$)$_4$ (8.4 mg, 0.006 mmol), DMF (3 mL) and water (0.75 mL). The vial was sealed and put in microwave reactor and heated for 15 min. at 120° C. Upon completion, the solvent was passed through Celite. The filtrate was concentrated under reduced pressure and the crude product purified by RP-HPLC to afford 109 mg of ethyl 3-(6-methoxypyridin-3-yl)-5-(trifluoromethyl)-1H-indole-2-carboxylate (79%): LC-MS>98% (214, 254 nm), Rt=1.190 min, m/z=364.8 [M+H]; $^1$H NMR (400 MHz, CDCl$_3$) 1.27 (t, J=7.1, 3H) 4.02 (s, 3H), 4.30-4.36 (q, J=7.1, 2H), 6.86-6.88 (dd, J=0.6, 8.5, 1H), 7.53-7.59 (m, 2H), 7.75-7.78 (dd, J=2.4, 8.5, 1H), 7.89 (d, J=0.6, 1H), 8.33-8.33 (dd, J=0.6, 2.4, 1H), 9.47 (s, 1H); $^{13}$C NMR (100.6 MHz, CDCl$_3$) 14.2, 53.7, 61.5, 110.3, 112.5, 119.4 (q, J=4.3), 121.2, 121.7, 122.5 (q, J=3.2), 123.8 (q, J=32.1), 125.0, 124.9 (q, J=271.0), 127.3, 136.9, 141.0, 147.9, 161.6, 163.7.

Step 2

To a vial was added ethyl 3-(6-methoxypyridin-3-yl)-5-(trifluoromethyl)-1H-indole-2-carboxylate (2 0 mg, 0.055 mmol), 3-methoxybenzyl bromide (14 mg, 0.082 mmol) and K$_2$CO$_3$ (15.2 mg, 0.110 mmol) and DMF (1.5 mL). The mixture was stirred for 6-8 h at 60° C. Upon completion, the desired indole ester was purified by the RP-HPLC to afford ethyl 1-(3-methoxybenzyl)-3-(6-methoxypyridin-3-yl)-5-(trifluoromethyl)-1H-indole-2-carboxylate (17 mg, 65%): LC-MS>95% (214, 254 nm), m/z=485.1 [M+H].

Step 3

To a solution of ethyl 1-(3-methoxybenzyl)-3-(6-methoxypyridin-3-yl)-5-(trifluoromethyl)-1H-indole-2-carboxylate (17 mg, 0.035 mmol) in THF was added lithium aluminum hydride (LAH) (1.0 M in THF) (70 μL, 0.07 mmol) at 0° C. The solution was allowed to warm to rt and stir for 45 min. Upon completion, 10 μL 2N HCl was added to consume the remaining LAH, followed by the addition of 10 μL saturated aq. NaHCO₃. The solvent was concentrated on a heated air-blowing block. The residue was purified by RP-HPLC to afford title example compound (Example B13) (10.2 mg, 65%): LC-MS>98% (214, 254 nm), Rt=1.232 min, m/z=442.8 [M+H].

Example 2

(Table 1, B75) (1-(2-chlorobenzyl)-3-(2-methoxy-imidazo[2,1-b][1,3,4]thiadiazol-6-yl)-5-(trifluoromethoxy)-1H-indol-2-yl)methanol

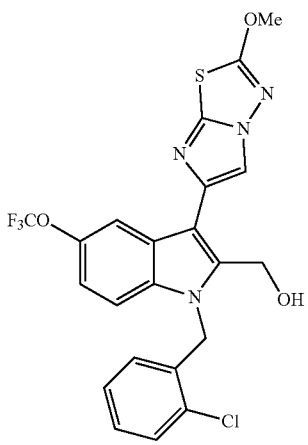 [SMILES: COc1nn2cc(-c3c(CO)n(Cc4ccccc4Cl)c4ccc(OC(F)(F)F)cc34)nc2s1]

Step 1. Preparation of ethyl 3-acetyl-5-(trifluoromethoxy)-1H-indole-2-carboxylate (2)

To an oven dried round bottom flask cooled under an Argon atmosphere was added a magnetic stirring bar and a solution of ethyl 5-(trifluoromethoxy)-1H-indole-2-carboxylate (1)(0.55 mmol) in 1,2-dichloroethane (2.2 mL). The solution was cooled to 0° C. where SnCl₄ (0.66 mmol) was added in a single portion via syringe. After the ice bath was removed, the mixture was stirred at ambient temperature for 30 minutes after which acetic anhydride (0.55 mmol) was added in small portions to the suspension followed by nitromethane (1.6 mL). The mixture was stirred for 48 hr at room temperature and then the reaction mixture was quenched with ice cooled water. The mixture was filtered to remove inorganic precipitates and the organic material was extracted with ethyl acetate (2×5 mL). The organic phase was dried over magnesium sulfate, concentrated, and purified via silica chromatography (hexanes-20% EtOAc/Hexanes) to afford title compound in 92% yield. M+H=316, RT 1.004.

¹H NMR (400 MHz, chloroform-d) δ 9.32 (s, 1H), 8.01 (s, 1H), 7.41-7.43 (d, J=8.92 Hz, 1H), 7.23-7.26 (m, 1H), 4.47-4.52 (q, J=7.15 Hz, 3H), 2.75 (s, 3H), 1.44-1.47 (t, J=7.14, 4H).

Step 2. Preparation of ethyl 3-|(2-chloroacetyl)-5-(trifluoromethoxy)-1H-indole-2-carboxylate (3)

Benzyltrimethylammonium dichloroiodate (0.81 mmol) was added to a solution of ethyl 3-acetyl-5-(trifluoromethoxy)-1H-indole-2-carboxylate (2) (0.54 mmol) in THF (1.8 mL) and the mixture was stirred at 50° C. for 3-5 hrs. Mixture was cooled to 0° C. and quenched with a 10% NaHCO₃ solution. The mixture is extracted with EtOAc (2×5 mL), washed with 5% Na₂S₂O₃(aq), brine, and the organic layer was dried with MgSO₄, filtered and evaporated at reduced pressure. Purification by silica chromatography (5% EtOAc/Hexanes-30% EtOAc/Hexanes) to afford the title compound in 83% yield. M+H=350, RT=1.217.

¹H NMR (400 MHz, chloroform-d) δ 9.31 (s, 1H), 8.06 (s, 1H), 7.44-7.46 (m, 1H), 7.27-7.7.30 (m, 1H), 4.91 (s, 2H), 4.49-4.54 (q, J=7.16 Hz, 3H), 1.46-1.50 (t, J=7.16, 4H).

Step 3. Preparation of ethyl 3-(2-bromoimidazo[2,1-b][1,3,4]thiadiazol-6-yl)-5-(trifluoromethoxy)-1H-indole-2-carboxylate (4)

Ethyl 3-(2-chloroacetyl)-5-(trifluoromethoxy)-1H-indole-2-carboxylate (3) was dissolveld in acetone (5.4 mmol) and NaBr (1.08 mmol) was added to the solution and the reaction mixture was stirred at 50° C. for 16 hr. Upon completion, the reaction was filtered, concentrated under reduced pressure and used directly in the next reaction. A mixture of ethyl 3-(2-bromoacetyl)-5-(trifluoromethoxy)-1H-indole-2-carboxylate (0.45 mmol) and 5-bromo-1,3,4-thiadiazol-2-amine (0.68 mmol) were dissolved in ACN/IPA (1:1; 5.6 mL) in a microwave vial that was sealed and heated to 80° C. for 18 hr. Next, the vial was placed in a Microwave for 30 minutes at 150° C. The reaction was diluted with DCM, washed with saturated sodium bicarb. (10 mL), brine, and dried over magnesium sulfate. Purification by silica chromatography (Hexanes30% EtOAc/Hexanes-80% EtOAc/Hexanes) afforded the title compound in 62% yield. M+H=476, RT=1.338.

¹H NMR (400 MHz, chloroform-d) δ 9.21 (s, 1H), 8.62 (s, 1H), 8.43-8.44 (m, 1H), 7.37-7.40 (d, J=8.92 Hz, 1H), 7.22-7.25 (m, 1H), 4.41-4.46 (q, J=7.14 Hz, 3H), 1.41-1.44 (t, J=7.14, 4H).

Step 4. Preparation of methyl 3-(2-methoxyimidazo[2,1-b][1,3,4]thiadiazol-6-yl)-5-(trifluoromethoxy)-1H-indole-2-carboxylate (5)

A solution of ethyl 3-(2-bromoimidazo[2,1-b][1,3,4]thiadiazol-6-yl)-5-(trifluoromethoxy)-1H-indole-2-carboxylate (4) (0.28 mmol) in a mixture of DCM/MeOH (4:1; 12.5 mL) was treated at 22° C. with a 25 wt. % solution of NaOMe (1.1 mmol) in MeOH. Next, an additional 2.5 mL of MeOH was added and the reaction was stirred fir 1 hr. Upon completion, the reaction mixture was quenched by addition of 1% HCl (5 mL) followed by addition of sat. NaHCO₃ (5 mL). Solvent was evaporated and the residue was diluted with DCM, washed with brine, dried with magnesium sulfate and evaporated. Column chromatography on silica (100% DCM-5% EtOAc/DCM-30% EtOAc/DCM) afforded title compound in 38% yield. M+H=413, RT=1.131.

¹H NMR (400 MHz, chloroform-d) δ 9.08 (s, 1H), 8.44 (s, 1H), 8.39 (s, 1H), 7.36-7.39 (d, J=8.88 Hz, 1H), 7.22-7.24 (d, J=8.76 Hz, 1H), 4.2165 (s, 1H), 3.96 (s, 1H).

Step 5. Preparation of methyl 1-(2-chlorobenzyl)-3-(2-methoxyimidazo[2,1-b][1,3,4]thiadiazol-6-yl)-5-(trifluoromethoxy)-1H-indole-2-carboxylate (6)

To a vial containing a magnetic stir bar were added methyl 3-(2-methoxyimidazo[2,1-b][1,3,4]thiadiazol-6-yl)-5-(trifluoromethoxy)-1H-indole-2-carboxylate (5) (0.02 mmol), potassium carbonate (0.05 mmol), and DMF (0.5 mL). Next, 2-chlorobenzyl bromide (0.05 mmol) was added and the reaction was stirred at ambient temperature for 16 hr. The reaction was then diluted with EtOAc (3 mL) and washed successively with 5% LiCl (2×5 mL) and brine. The organic layer was then dried over magnesium sulfate, filtered and concentrated. Column chromatography on silica (Hexanes-25% EtOAc/Hexanes) afforded title compound in 30% yield. M+H=536, RT=1.268

Step 6. Preparation of (1-(2-chlorobenzyl)-3-(2-methoxyimidazo[2,1-b][1,3,4]thiadiazol-6-yl)-5-(trifluoromethoxy)-1H-indol-2-yl)methanol (7)

To vial were added methyl 1-(2-chlorobenzyl)-3-(2-methoxyimidazo[2,1-b][1,3,4]thiadiazol-6-yl)-5-(trifluoromethoxy)-1H-indole-2-carboxylate (6) (0.006 mmol) in THF (1.5 mL) followed by LiBH$_4$ (0.014 mmol) at room temperature. The mixture was allowed to stir for 16 hr and then quenched by addition of Glauber's salt, filtered, and concentrated. Column chromatography on silica (10% EtOAc/Hexanes-25% EtOAc/Hexanes-50% EtOAc/Hexanes) afforded title compound in 43% yield. M+H=454; RT=1.093

$^1$H NMR (400 MHz, chloroform-d) δ 7.92 (s, 1H), 7.65 (s, 1H), 7.42-7.44 (dd, J$_1$=0.98 Hz, J$_2$=7.94 Hz, 1H), 7.18-7.23 (m, 2H), 7.04-7.10 (m, 2H), 6.43-6.45 (d, J=7.40 Hz, 1H), 5.73 (s, 1H), 5.56 (s, 2H), 4.76 (s, 2H), 4.24 (s, 3H).

TABLE 1

I.

| No. | Compound | LC-MS [M + H] | Retention time | Synthetic Example/ Scheme* |
|---|---|---|---|---|
| B1 |  | 447 | 1.034 | Intermediate A1/Ex. 1/ Scheme 1 |
| B2 |  | 465 | 1.075 | Intermediate A1/Ex. 1/ Scheme 1 |

TABLE 1-continued
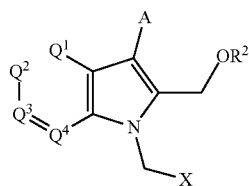
I.
| No. | Compound | LC-MS [M + H] | Retention time | Synthetic Example/ Scheme* |
|---|---|---|---|---|
| B3 | | 497 | 1.105 | Intermediate A1/Ex. 1/ Scheme 1 |
| B4 | | 429 | 1.095 | Intermediate A1/Ex. 1/ Scheme 1 |
| B5 | | 465 | 1.145 | Intermediate A1/Ex. 1/ Scheme 1 |

TABLE 1-continued
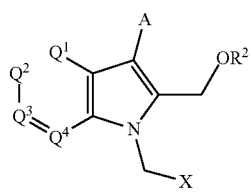
I.
| No. | Compound | LC-MS [M + H] | Retention time | Synthetic Example/ Scheme* |
|---|---|---|---|---|
| B6 | | 447 | 1.136 | Intermediate A1/Ex. 1/ Scheme 1 |
| B7 | | 507 | 1.272 | Intermediate A1/Ex. 1/ Scheme 1 |
| B8 | | 353 | 1.095 | Intermediate A1/Ex. 1/ Scheme 1 |

TABLE 1-continued
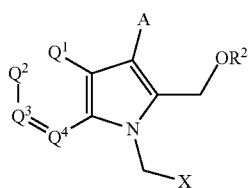
I.
| No. | Compound | LC-MS [M + H] | Retention time | Synthetic Example/ Scheme* |
|---|---|---|---|---|
| B9 | | 463 | 1.205 | Intermediate A1/Ex. 1/ Scheme 1 |
| B10 | | 489 | 1.255 | Intermediate A1/Ex. 1/ Scheme 1 |
| B11 | | 459 | 1.191 | Intermediate A1/Ex. 1/ Scheme 1 |

TABLE 1-continued
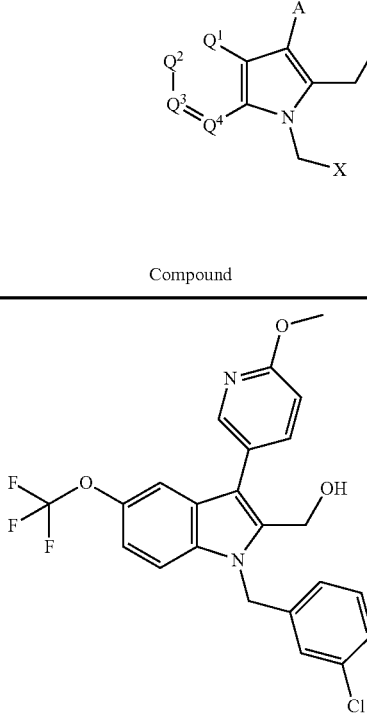
| No. | Compound | LC-MS [M + H] | Retention time | Synthetic Example/ Scheme* |
|---|---|---|---|---|
| B12 | | 463 | 1.216 | Intermediate A1/Ex. 1/ Scheme 1 |
| B13 | | 443 | 1.132 | Intermediate A2/Ex. 1/ Scheme 2 |
| B14 | | 414 | 1.055 | Intermediate A2/Ex. 1/ Scheme 2 |

TABLE 1-continued

I.

| No. | Compound | LC-MS [M + H] | Retention time | Synthetic Example/ Scheme* |
|---|---|---|---|---|
| B15 | 3-(6-methoxypyridin-3-yl)-1-benzyl-7-azaindol-2-yl)methanol | 346 | 0.980 | Intermediate A2/Ex. 1/ Scheme 2 |
| B16 | 3-(6-methoxypyridin-3-yl)-1-(3-methoxybenzyl)-7-azaindol-2-yl)methanol | 376 | 0.988 | Intermediate A2/Ex. 1/ Scheme 2 |
| B17 | 3-(6-methoxypyridin-3-yl)-1-(3-bromobenzyl)-7-azaindol-2-yl)methanol | 426 | 0.995 | Intermediate A2/Ex. 1/ Scheme 2 |

TABLE 1-continued
I.
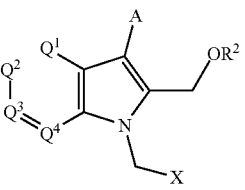
| No. | Compound | LC-MS [M + H] | Retention time | Synthetic Example/ Scheme* |
|---|---|---|---|---|
| B18 | 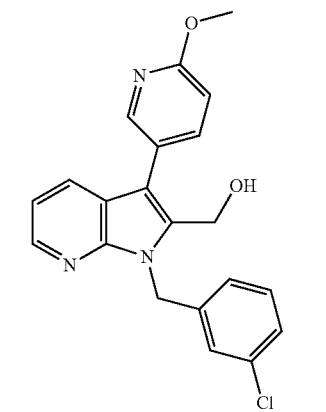 [SMILES: COc1ccc(-c2c(CO)n(Cc3cccc(Cl)c3)c3ncccc23)cn1] | 380 | 0.959 | Intermediate A2/Ex. 1/ Scheme 2 |
| B19 | 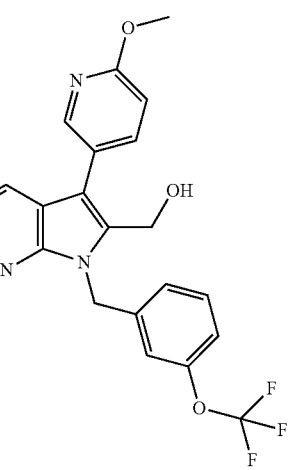 | 430 | 1.050 | Intermediate A2/Ex. 1/ Scheme 2 |
| B20 |  | 364 | 0.985 | Intermediate A2/Ex. 1/ Scheme 2 |

TABLE 1-continued
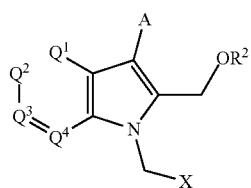
I.
| No. | Compound | LC-MS [M + H] | Retention time | Synthetic Example/ Scheme* |
|---|---|---|---|---|
| B21 | | 503 | 0.989 | Intermediate A1/Ex. 1/ Scheme 1 |
| B22 | | 507 | 0.923 | Intermediate A1/Ex. 1/ Scheme 1 |
| B23 | | 441 | 1.005 | Intermediate A1/Ex. 1/ Scheme 1 |

TABLE 1-continued

I.

| No. | Compound | LC-MS [M + H] | Retention time | Synthetic Example/ Scheme* |
|---|---|---|---|---|
| B24 | | 370 | 1.215 | Intermediate A1/Ex. 1/ Scheme 1 |
| B25 | | 453 | 0.985 | Intermediate A1/Ex. 1/ Scheme 1 |
| B26 | | 371 | 0.866 | Intermediate A1/Ex. 1/ Scheme 1 |

TABLE 1-continued
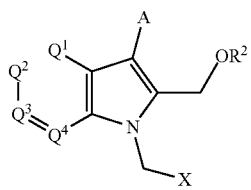
I.
| No. | Compound | LC-MS [M + H] | Retention time | Synthetic Example/ Scheme* |
|---|---|---|---|---|
| B27 | 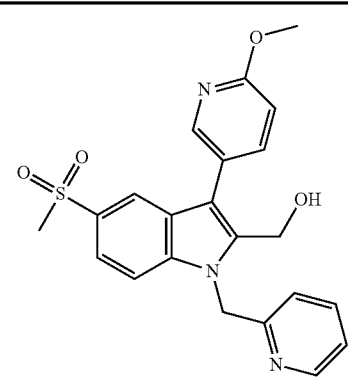 | 424 | 0.82 | Intermediate A1/Ex. 1/ Scheme 1 |
| B28 | 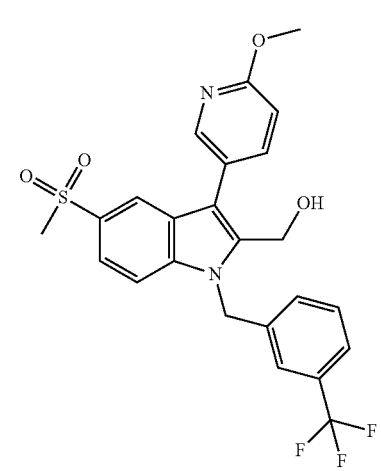 [SMILES: COc1ccc(-c2c(CO)n(Cc3cccc(C(F)(F)F)c3)c3ccc(S(C)(=O)=O)cc23)cn1] | 400 | 1.055 | Intermediate A1/Ex. 1/ Scheme 1 |
| B29 | | 491 | 1.152 | Intermediate A1/Ex. 1/ Scheme 1 |

TABLE 1-continued
I.
| No. | Compound | LC-MS [M + H] | Retention time | Synthetic Example/ Scheme* |
|---|---|---|---|---|
| B30 | 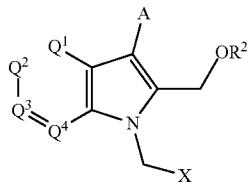 | 457 | 1.205 | Intermediate A1/Ex. 1/ Scheme 1 |
| B31 | 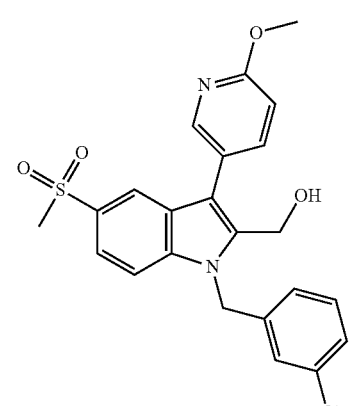 | 448 | 1.178 | Intermediate A1/Ex. 1/ Scheme 1 |
| B32 | 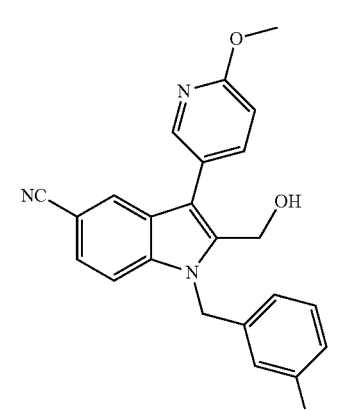 | 454 | 1.213 | Intermediate A1/Ex. 1/ Scheme 1 |

TABLE 1-continued
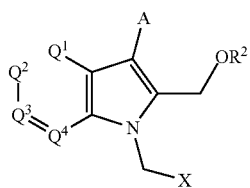
I.
| No. | Compound | LC-MS [M + H] | Retention time | Synthetic Example/ Scheme* |
|---|---|---|---|---|
| B33 | | 406 | 1.142 | Intermediate A1/Ex. 1/ Scheme 1 |
| B34 | | 404 | 1.161 | Intermediate A1/Ex. 1/ Scheme 1 |
| B35 | | 438 | 1.19 | Intermediate A1/Ex. 1/ Scheme 1 |

TABLE 1-continued

I.

| No. | Compound | LC-MS [M + H] | Retention time | Synthetic Example/ Scheme* |
|---|---|---|---|---|
| B36 | | 413 | 1.086 | Intermediate A1/Ex. 1/ Scheme 1 |
| B37 | | 389 | 1.049 | Intermediate A2/Ex. 1/ Scheme 2 |
| B38 | | 390 | 0.833 | Intermediate A2/Ex. 1/ Scheme 2 |

TABLE 1-continued
I.
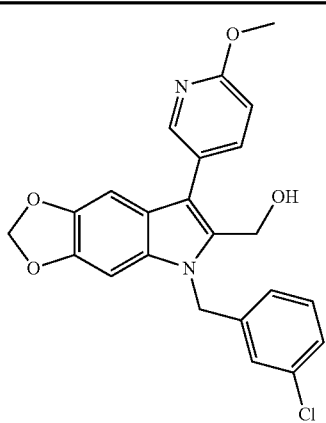
| No. | Compound | LC-MS [M + H] | Retention time | Synthetic Example/ Scheme* |
|---|---|---|---|---|
| B39 | 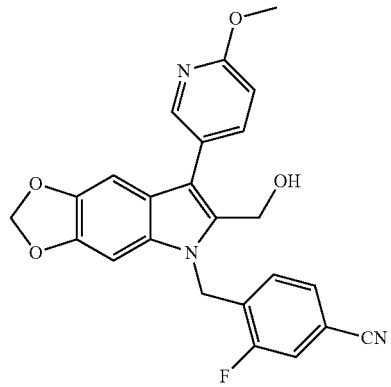 [SMILES: COc1ccc(-c2c(CO)n(Cc3ccc(C#N)cc3F)c3cc4c(cc23)OCO4)cn1] | 423 | 1.17 | Intermediate A2/Ex. 1/ Scheme 2 |
| B40 | 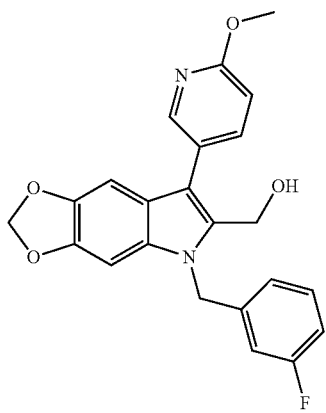 [SMILES: COc1ccc(-c2c(CO)n(Cc3cccc(F)c3)c3cc4c(cc23)OCO4)cn1] | 432 | 1.049 | Intermediate A2/Ex. 1/ Scheme 2 |
| B41 | | 407 | 1.119 | Intermediate A2/Ex. 1/ Scheme 2 |

TABLE 1-continued
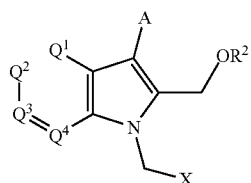
I.
| No. | Compound | LC-MS [M + H] | Retention time | Synthetic Example/ Scheme* |
|---|---|---|---|---|
| B42 | | 457 | 1.139 | Intermediate A2/Ex. 1/ Scheme 2 |
| B43 | | 423 | 1.711 | Intermediate A2/Ex. 1/ Scheme 2 |
| B44 | | 469 | 1.159 | Intermediate A2/Ex. 1/ Scheme 2 |

TABLE 1-continued

I.

| No. | Compound | LC-MS [M + H] | Retention time | Synthetic Example/ Scheme* |
|---|---|---|---|---|
| B45 | | 419 | 1.059 | Intermediate A2/Ex. 1/ Scheme 2 |
| B46 | | 425 | 1.147 | Intermediate A2/Ex. 1/ Scheme 2 |
| B47 | | 433 | 1.057 | Intermediate A1/Ex. 1/ Scheme 1 |

TABLE 1-continued
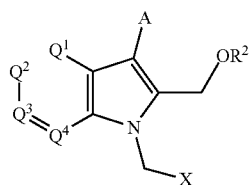
| No. | Compound | LC-MS [M + H] | Retention time | Synthetic Example/ Scheme* |
|---|---|---|---|---|
| B48 | | 466 (M—OH) | 1.306 | Intermediate A1/Ex. 1/ Scheme 1 |
| B49 | | 420 (M—OH) | 1.297 | Intermediate A1/Ex. 1/ Scheme 1 |
| B50 | | 480 | 1.037 | Intermediate A1/Ex. 1/ Scheme 1 |

TABLE 1-continued
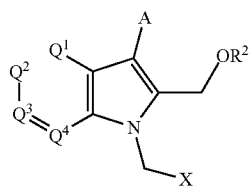
| No. | Compound | LC-MS [M + H] | Retention time | Synthetic Example/ Scheme* |
|---|---|---|---|---|
| B51 | | 464 (M—OH) | 1.428 | Intermediate A1/Ex. 1/ Scheme 1 |
| B52 | | 478 | 1.042 | Intermediate A1/Ex. 1/ Scheme 1 |
| B53 | | 453 | 1.332 | Intermediate A1/Ex. 1/ Scheme 1 |

TABLE 1-continued

I.

[Structure: pyrrole core with substituents A, Q¹, Q², Q³, Q⁴, OR², N-CH₂-X]

| No. | Compound | LC-MS [M + H] | Retention time | Synthetic Example/ Scheme* |
|-----|----------|---------------|----------------|----------------------------|
| B54 | [2-methoxypyrimidin-5-yl at indole C3; F₃CO at indole 5-position; 2-CH₂OH; N-(2-chlorobenzyl)] | 464 | 1.027 | Intermediate A1/Ex. 1/ Scheme 1 |
| B55 | [pyrimidin-5-yl at indole C3; F₃CO at indole 5-position; 2-CH₂OH; N-(2-chlorobenzyl)] | 434 | 1.016 | Intermediate A1/Ex. 1/ Scheme 1 |
| B56 | [2-methoxypyrimidin-5-yl at indole C3; F₃CO at indole 5-position; 2-CH₂OH; N-(2,4-difluorobenzyl)] | 450 (M—OH) | 1.384 | Intermediate A1/Ex. 1/ Scheme 1 |

TABLE 1-continued
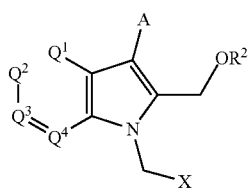
I.
| No. | Compound | LC-MS [M + H] | Retention time | Synthetic Example/ Scheme* |
|---|---|---|---|---|
| B57 | | 451 | 1.342 | Intermediate A1/Ex. 1/ Scheme 1 |
| B58 | | 435 | 1.068 | Intermediate A1/Ex. 1/ Scheme 1 |
| B59 | | 409 | 1.100 | Intermediate A2/Ex. 1/ Scheme 2 |

TABLE 1-continued
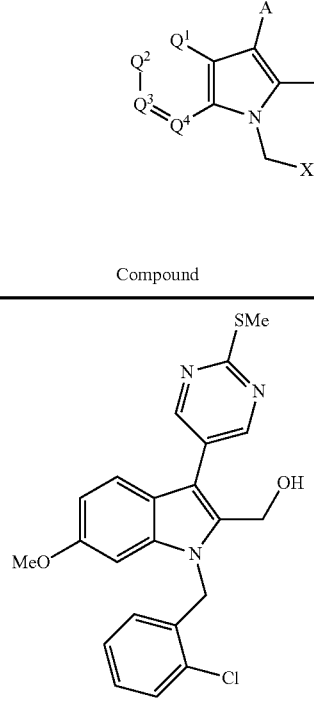
| No. | Compound | LC-MS [M + H] | Retention time | Synthetic Example/ Scheme* |
|---|---|---|---|---|
| B60 | | 426 | 1.118 | Intermediate A2/Ex. 1/ Scheme 2 |
| B61 | | 423 | 1.135 | Intermediate A2/Ex. 1/ Scheme 2 |
| B62 | | 429 | 1.187 | Intermediate A2/Ex. 1/ Scheme 2 |

TABLE 1-continued
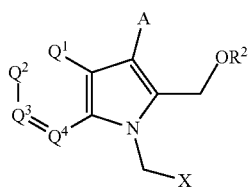
| No. | Compound | LC-MS [M + H] | Retention time | Synthetic Example/ Scheme* |
|---|---|---|---|---|
| B63 | 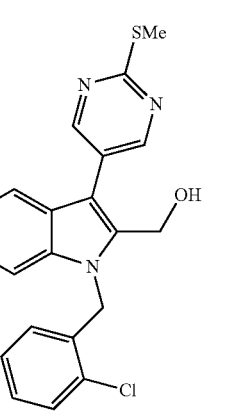 | 440 | 1.197 | Intermediate A2/Ex. 1/ Scheme 2 |
| B64 | 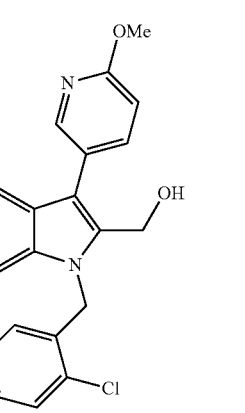 | 454 | 1.184 | Intermediate A2/Ex. 1/ Scheme 2 |
| B65 |  | 463 | 1.191 | Intermediate A2/Ex. 1/ Scheme 2 |

TABLE 1-continued
I.
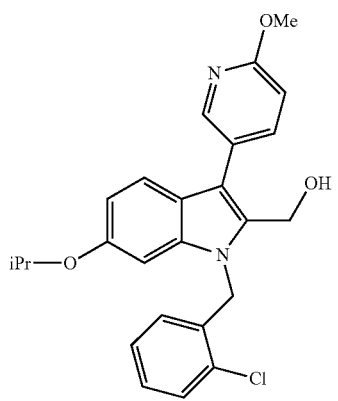 [SMILES: COc1ccc(-c2c(CO)n(Cc3ccccc3Cl)c3cc(OC(C)C)ccc23)cn1]
| No. | Compound | LC-MS [M + H] | Retention time | Synthetic Example/ Scheme* |
|---|---|---|---|---|
| B66 | 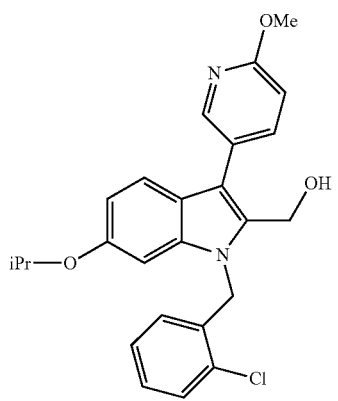 [SMILES: COc1ccc(-c2c(CO)n(Cc3ccccc3Cl)c3cc(OC(C)C)ccc23)cn1] | 437 | 1.13 | Intermediate A2/Ex. 1/ Scheme 2 |
| B67 | 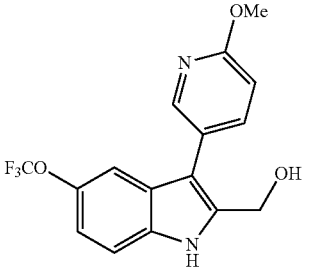 [SMILES: COc1ccc(-c2c(CO)[nH]c3ccc(OC(F)(F)F)cc23)cn1] | 339 | 1.011 | |
| B68 | 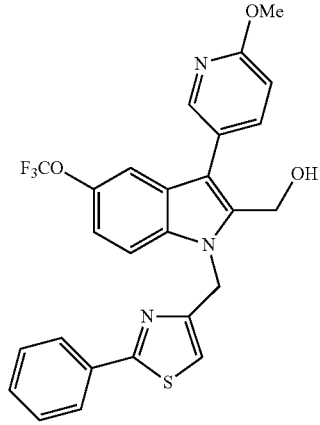 [SMILES: COc1ccc(-c2c(CO)n(Cc3csc(-c4ccccc4)n3)c3ccc(OC(F)(F)F)cc23)cn1] | 514 | 1.225 | Intermediate A1/Ex. 1/ Scheme 1 |

TABLE 1-continued
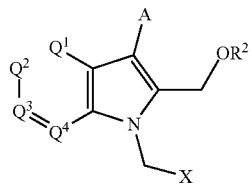
I.
| No. | Compound | LC-MS [M + H] | Retention time | Synthetic Example/ Scheme* |
|---|---|---|---|---|
| B69 | | 512 | 1.218 | Intermediate A1/Ex. 1/ Scheme 1 |
| B70 | | 511.7 (loss of methyl-2-phenylthiazole) | 1.1213 | Intermediate A1/Ex. 1/ Scheme 1, 3-4 |
| B71 | | 480 | 1.216 | Intermediate A2/Ex. 1/ Scheme 2 |

TABLE 1-continued
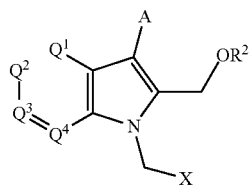
| No. | Compound | LC-MS [M + H] | Retention time | Synthetic Example/ Scheme* |
|---|---|---|---|---|
| B72 | | 403 | 1.079 | Intermediate A2/Ex. 1/ Scheme 2 |
| B73 | | 460 | 1.100 (non-polar method) | Intermediate A2/Ex. 1/ Scheme 2 |
| B74 | | 435 | 0.926 | Intermediate A2/Ex. 2/ Scheme 4-5 |

TABLE 1-continued

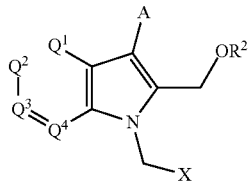

I.

| No. | Compound | LC-MS [M + H] | Retention time | Synthetic Example/ Scheme* |
|---|---|---|---|---|
| B75 | | 590 | 0.948 | Intermediate A2/Ex. 2/ Scheme 4-5 |
| B76 | | 480 | 1.396 | Intermediate A2/Ex. 1/ Scheme 2 |

3. Assay Descriptions

PAC-1 Binding assay: 60 μL of washed platelets (Tyrodes buffer containing 0.1% BSA) at a concentration of $0.15 \times 10^8$ platelets/mL were added to 5 mL round bottom polystyrene tubes (BD, Franklin Lakes, N.J.). FITC conjugated PAC-1 (BD Biosciences, San Jose, Calif.) antibody was diluted (to the manufacturers recommended concentration) in Tyrode's buffer containing 0.1% BSA. 40 μL of diluted antibody was added to the platelets and allowed to incubate for 5 minutes. Platelets were pre-treated with indicated concentrations of antagonist or DMSO control for 5 minutes followed by addition of PAR1-AP (GL Biochem, Shanghai, China) or PAR4-AP for 10 minutes. Platelet activity was quenched by the addition of ice cold 1.5% paraformaldehyde followed by dilution in 1× phosphate buffered saline. The final DMSO concentration was 0.5%. Platelets were stored up to 18 hours at 4° C. before flow cytometric analysis. Analysis was carried out on a BD FACS Canto II (Franklin Lakes, N.J.). Fluorescent intensity was determined for 100,000 events within the platelet gate. Data was collected and analyzed via FACS DiVa software. Flow cytometric data analysis was conducted by the following method. The DMSO-vehicle treated control was subtracted from each data point. 100% response for PAR4-AP was determined for each individual as the DMSO treated control stimulated with either 200 μM PAR4-AP, or 20 μM PAR1-AP. Data was plotted in Graph-Pad PRISM v.5.0. For compounds with a notable reduction in PAC-1 binding response, dose response curves and $IC_{50}$ values were generated using the inhibitory sigmoidal dose response 'variable slope' parameter. PAR4 results are plotted as mean values.

4. In Vitro Activity of Representative PAR4 Antagonists.

TABLE 2

| Example | % Max PAC-1/IC$_{50}$ [M] |
|---|---|
| B1 | 80.6 |
| B2 | 19.7/8.23E−07 |
| B3 | 59.7 |
| B4 | 53.4 |
| B5 | 36.5 |
| B6 | 89.0 |
| B7 | 27.2 |
| B8 | 93.9 |
| B9 | 21.4/6.58E−07 |
| B10 | 110.6 |
| B11 | 40.9 |
| B12 | 27.8 |
| B13 | 108.5 |
| B14 | 49.5 |
| B15 | 109.0 |
| B16 | 69.0 |
| B17 | 76.2 |
| B18 | 80.6 |
| B19 | 42.9/1.0E−05 |
| B20 | 97.5 |
| B21 | 74.3 |
| B22 | 87.4 |
| B23 | 84.6 |
| B24 | 83.9 |
| B25 | 77.5 |
| B26 | 113.7 |
| B27 | 100.1 |
| B28 | 82.3 |
| B29 | 88.6 |
| B30 | 77.7 |
| B31 | 109.1 |
| B32 | 114.3 |
| B33 | 105.0 |
| B34 | 85.4 |
| B35 | 90.5 |
| B36 | 108.8 |
| B37 | 80.7 |
| B38 | 107.2 |
| B39 | 100.1 |
| B40 | 98.6 |
| B41 | 61.9 |
| B42 | 71.3 |
| B43 | 83.6 |
| B44 | 96.5 |
| B45 | 129.1 |
| B46 | 94.7 |
| B47 | 101.7 |
| B48 | 14.5/1.98E−06 |
| B49 | 96.0 |
| B50 | 4.68/5.51E−07 |
| B51 | 48.5 |
| B52 | 24.0 |
| B53 | 48.2 |
| B54 | 2.01/2.9E−06 |
| B55 | 101.8 |
| B56 | 53.7/>1.0E−05 |
| B57 | 21.05/1.29E−06 |
| B58 | 102.2 |
| B59 | 4.31/1.35E−06 |
| B60 | 21.33/4.30E−06 |
| B61 | 19.78/3.84E−06 |
| B62 | 34.32/3.71E−06 |
| B63 | 14.77/2.15E−06 |
| B64 | 18.53/1.38E−06 |
| B65 | 12.25/9.66E−07 |
| B66 | 59.45 |
| B67 | 116.1 |
| B68 | 61.98 |
| B69 | 89.19 |
| B70 | 61.82 |
| B71 | 5.57/1.62E−07 |
| B72 | 81.76 |

TABLE 2-continued

| Example | % Max PAC-1/IC$_{50}$ [M] |
|---|---|
| B73 | 107.63 |
| B74 | 38.32 |
| B75 | 8.40/1.84E−07 |
| B76 | 79.22 |

F. REFERENCES

1. Ruggeri, Z. M. *Platelets in atherothrombosis. Nat. Med.* 2002, 8, 1227-1234.
2. Adams, M. N.; Ramachandran, R.; Yau, M.-K.; Suen, J. Y.; Fairlie, D. P.; Hollenberg, M. D.; Hooper, J. D. *Pharm. Therap.* 2011, 130, 248-282.
3. Coughlin, S. *Nature* 2000, 407, 258-322.
4. Kahn, M. L.; Zheng, Y. W.; Huang, W.; Bigornia, V.; Zeng, D.; Moff, S.; Farese, R. V., Jr.; Tam, C.; Coughlin, S. R. *Nature* 1998, 394, 690-694.
5. Mao, Y.; Zhang, M.; Tuma, R.; Kunapuli, S. *Journal of cerebral blood flow and metabolism* 2010, 30, 1044-1096.
6. Vandendries, E. R.; Hamilton, J. R.; Coughlin, S. R.; Furie, B.; Furie, B. C. *Proc. Nat. Acad. Sci. USA* 2007, 104, 288-292.
7. Cornelissen, I.; Palmer, D.; David, T.; Wilsbacher, L.; Concengco, C.; Conley, P.; Pandey, A.; Coughlin, S. R. *Proc. Nat. Acad. Sci. USA* 2010, 107, 18605-18615.
8. Sambrano, G.; Weiss, E.; Zheng, Y.; Huang, W.; Coughlin, S. *Nature* 2001, 413, 7 4-82.
9. Henrih-Noack, P.; Riek-Burchardt, M.; Baldauf, K.; Reiser, G.; Reymann, K. Brain *Research* 2006, 1070, 232-273.
10. See http://www.mercknewsroom.com and http://www.fda.gov for May 2014 Zontivity™ press releases.
11. For information on the MLPCN and information on how to request probe compounds, such as ML354, see: http://mli.nih.gov/mli/mlpcn/.
12. Lee, F.-Y.; Lien, J.-C.; Huang, L.-J.; Huang, T.-M.; Tsai, S.-C.; Teng, C.-M.; Wu, C.-C.; Cheng, F.-C.; Kuo, S.-C. *J. Med. Chem.* 2001, 44, 3746-3755.
13. Chen, H.-S.; Kuo, S.-C.; Teng, C.-M.; Lee, F.-Y.; Want, J.-P.; Lee, Y.-C.; Kuo, C.-W.; Huang, C.-C.; Wu, C.-C.; Huang, L.-J. *Bioorg. Med. Chem.* 2008, 16, 1262-1340.
14. Young, S. E.; Duvernay, M. T.; Schulte, M. L.; Lindsley, C. W.; Hamm, H. E. *PLoS One* 2013, 8, e65528.
15. Smith, G. F. *Progress in Medicinal Chemistry* 2011, 50, 1-47.
16. Kou-San, J. *Microbiology and Molecular Biology Reviews* 2012, 74, 250-272.
17. Cai, Q.; Li, Z.; Wei, J.; Ha, C.; Pei, C.; Ding, K. *Chem. Commun.* 2009, 7581-7583.
18. Meanwell, N. A. *J. Med. Chem.* 2011, 54, 2529-2591.

We claim:

1. A compound having a structure represented by formula (I):

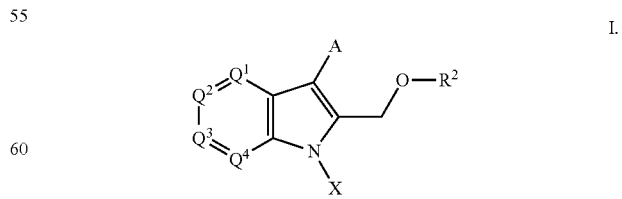

wherein:
Q$^1$ is selected from N and CR$^{1a}$;
Q$^2$ is selected from N and CR$^{1b}$, or can optionally cyclize with Q$^3$ to form a C5 or C6 saturated heterocycle;

$Q^3$ is selected from N and $CR^{1c}$, or can optionally cyclize with $Q^2$ to form a C5 or C6 saturated heterocycle;

$Q^4$ is selected from N and $CR^{1d}$; and wherein 0, 1, or 2 of $Q^1$, $Q^2$, $Q^3$ and $Q^4$ are N;

$R^{1a}$, $R^{1b}$, $R^{1c}$, and $R^{1d}$, when present, are each independently selected from hydrogen, halogen, hydroxyl, cyano, $C_1$-$C_3$ alkyl sulfone, $C_1$-$C_3$ polyhaloalkyl sulfone, $C_1$-$C_6$ alkyl, $C_1$-$C_6$ haloalkyl, $C_1$-$C_6$ polyhaloalkyl, $C_1$-$C_6$ alkoxy, ($C_1$-$C_6$) alkoxy-($C_1$-$C_6$) alkyl, ($C_1$-$C_6$) alkylamino, ($C_1$-$C_6$) haloalkyl-oxy-($C_1$-$C_6$) alkyl, ($C_1$-$C_6$) polyhaloalkyl-oxy-($C_1$-$C_6$) alkyl, ($C_1$-$C_6$) polyhaloalkyl-($C_1$-$C_6$) alkoxy, and ($C_1$-$C_6$) dialkylamino; n is 0-5;

X is independently selected from optionally substituted $CH_2$-aryl, $CH_2$-heteroaryl, $CH_2$-biaryl, or

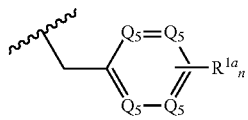

wherein:
$Q^5$ is selected from N, $CR^{1a}$, and $R^{1a}$; and
n is 0-5;
$R^2$ is selected from hydrogen, $C_1$-$C_3$ alkyl, $C_1$-$C_3$ haloalkyl, and $C_1$-$C_3$ polyhaloalkyl, ($C_1$-$C_3$) polyhaloalkyl-oxy-($C_1$-$C_3$) alkyl, and ($C_1$-$C_3$) haloalkyl-oxy-($C_1$-$C_3$) alkyl, and A is optionally substituted and chosen from imidazolyl, oxadiazolyl, oxazolyl, pyrazinyl, pyrazolyl, pyridinyl, pyrimidinyl, thiadiazolyl, thiazolyl, imidazothiadiazolyl, imidazooxadiazole, imidazothiazole, thiazolotriazole, and triazolyl;

or a pharmaceutically acceptable salt, solvate, or polymorph thereof.

2. A compound of claim 1, wherein $R^2$ is hydrogen.

3. A compound of claim 1, wherein $Q^2$ or $Q^3$ is substituted with C—O—$CF_3$.

4. A compound of claim 1, wherein A is pyridinyl, pyrimidinyl, or imadazothiadiazolyl, imidazooxadiazole, thiazolotriazole, imidazothiazole.

5. A compound of claim 1, wherein A is pyridinyl.

6. A compound of claim 5, wherein A is of the following formula;

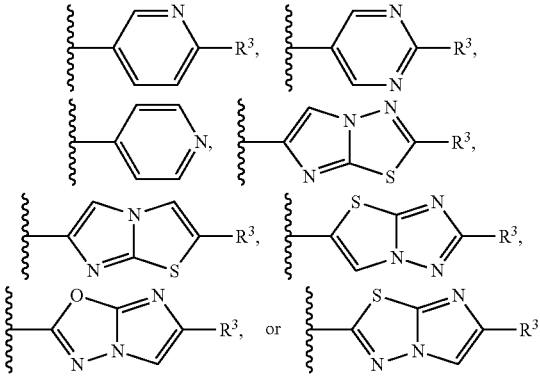

wherein:
$R^3$ is selected from —O—$CH_3$, halogen, —S—$CH_3$, hydrogen, or —O—$CH_2CH_3$.

7. A compound of claim 1, wherein A is substituted with alkoxy, thioether, or halogen.

8. A compound of claim 1, wherein $R^2$ is selected from hydrogen or phenylthiazolymethyl.

9. A compound of claim 1, (I), wherein $Q^2$ cyclizes with $Q^3$ to form dioxolane.

10. A compound of claim 1 of the following formula:

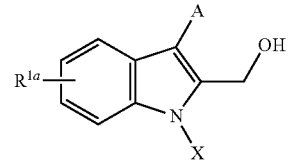

wherein:
X is $CH_2$—$R^4$;
$R^4$ is substituted or unsubstituted phenyl, pyridinyl, phenyldihydrothiazolyl or phenylthiazolyl.

11. A compound of claim 1 of the following formula:

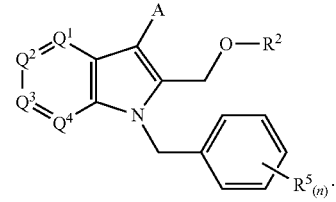

12. A compound of claim 11 wherein $Q^4$ is N;
$R^5$ is selected from hydrogen, Cl, Br, F, cyano, O—$CF_3$, —O—$CH_3$, or $CF_3$; and n is 0-2.

13. A compound of claim 1, of the following formula:

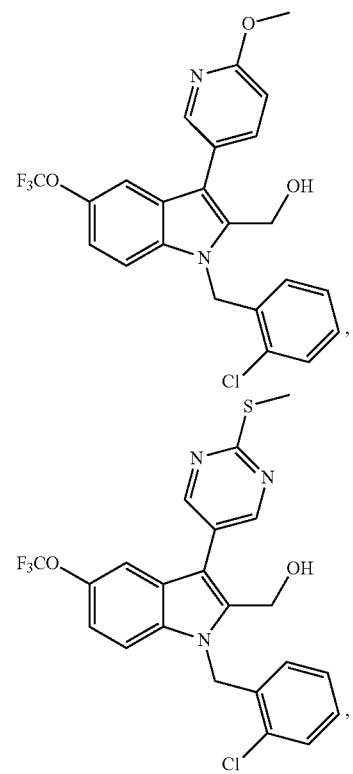

111
-continued
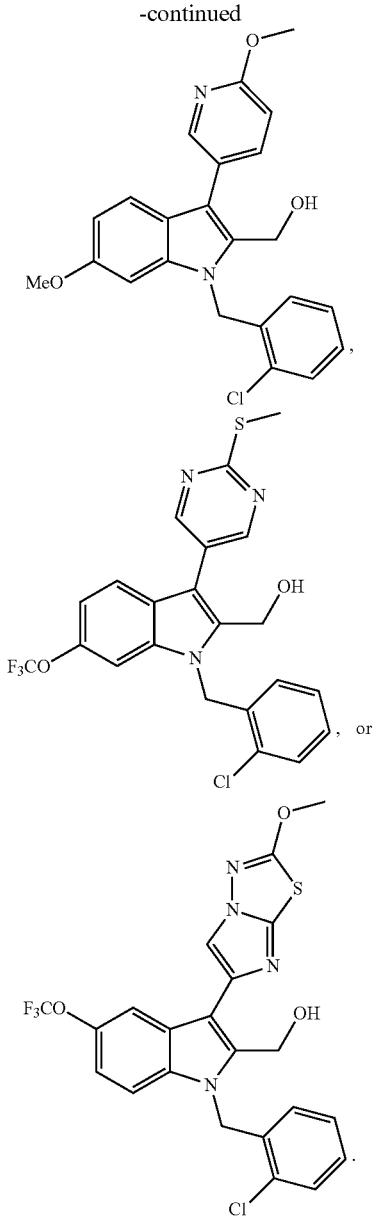
14. A compound of claim 1, of the following formula:
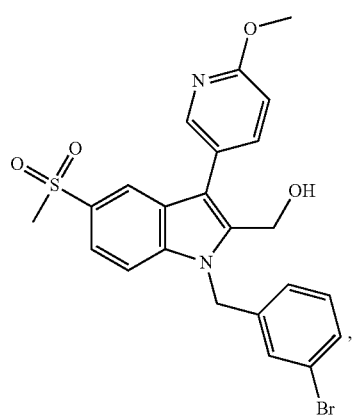
112
-continued
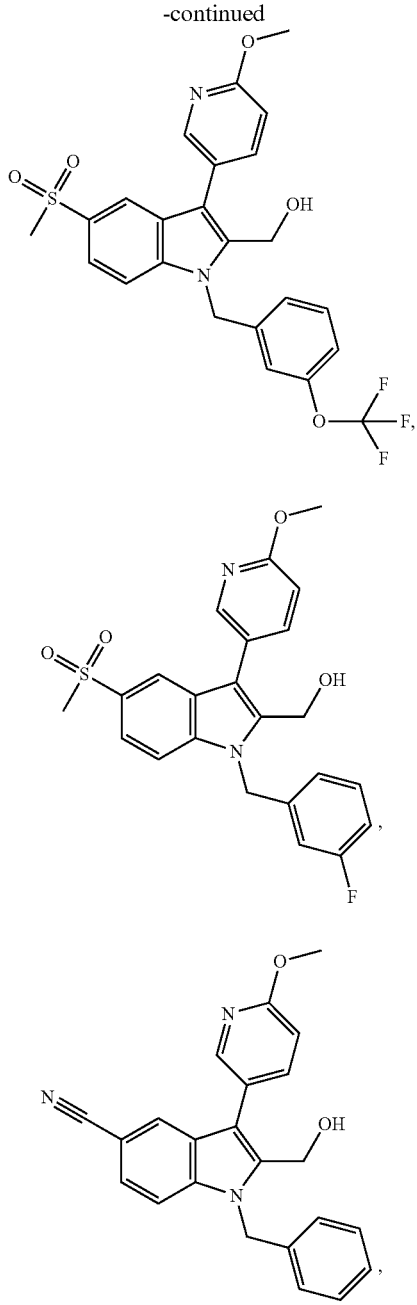
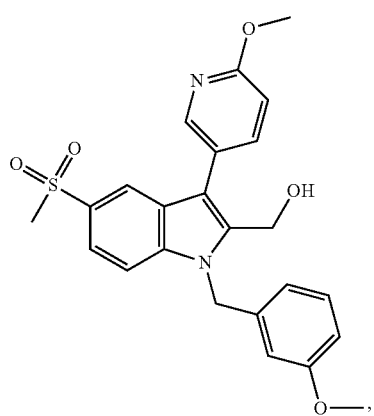

113
-continued
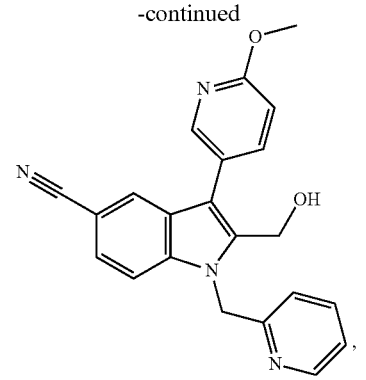
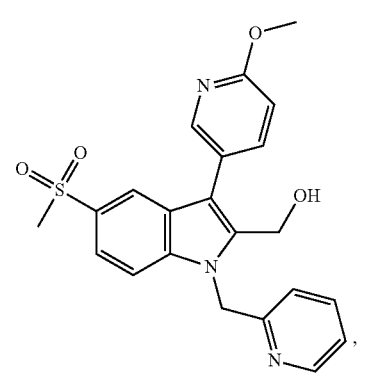
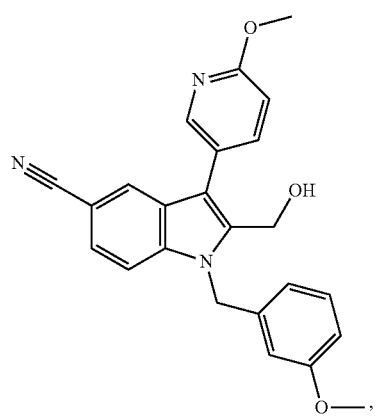
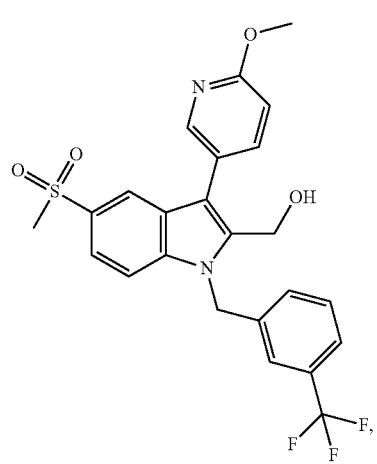
114
-continued
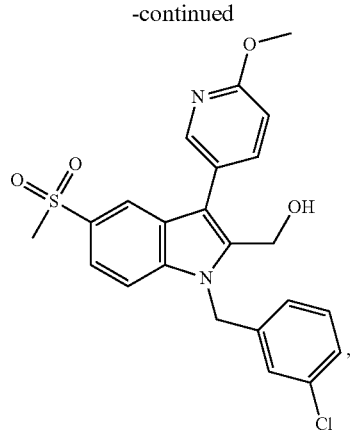
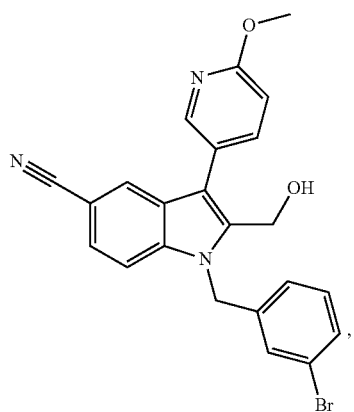
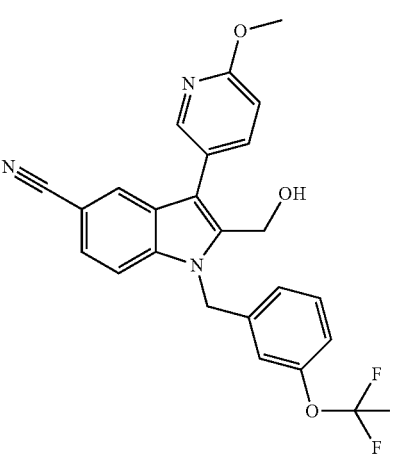
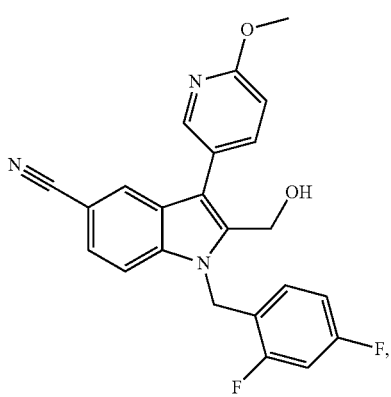

115
-continued
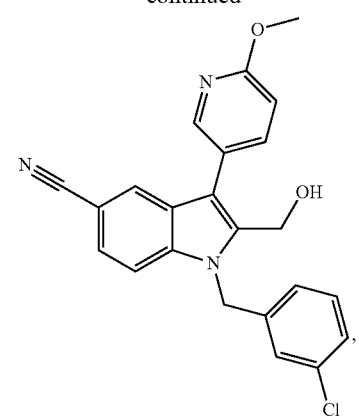
116
-continued
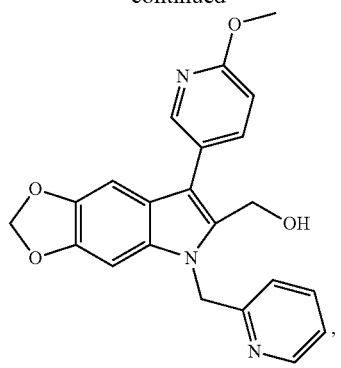
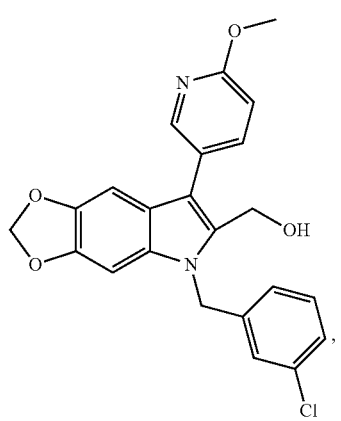
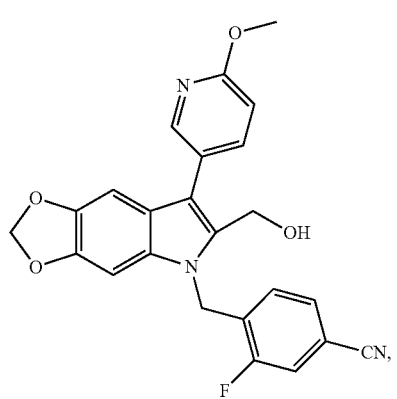
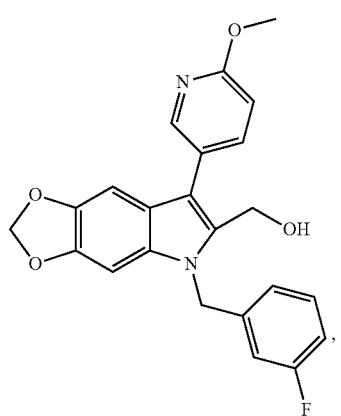

117
-continued
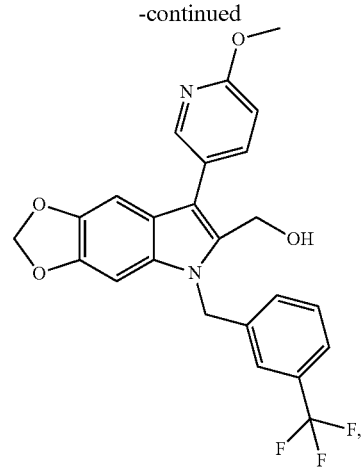
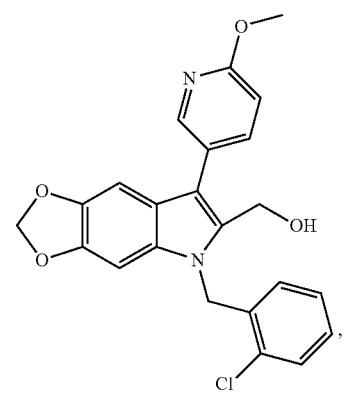
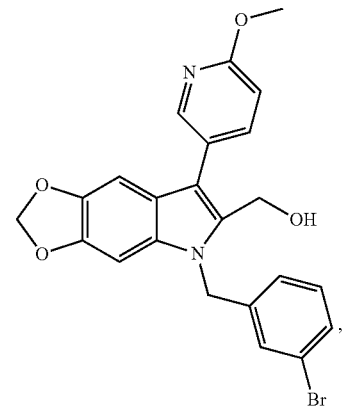
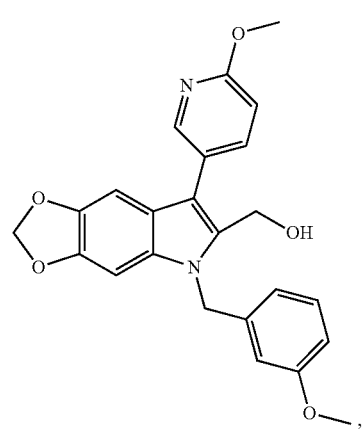
118
-continued
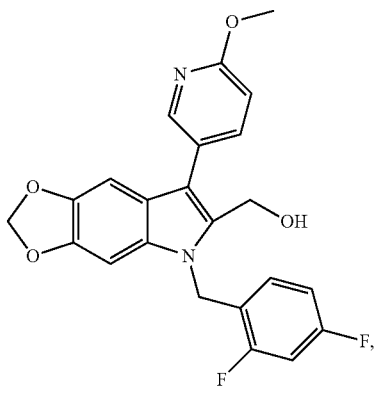
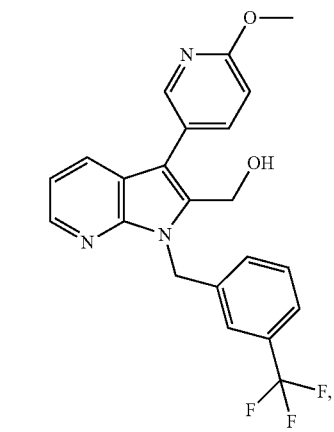
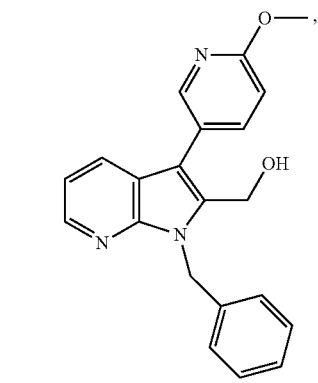
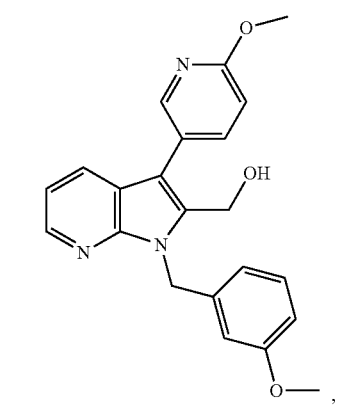

119
-continued
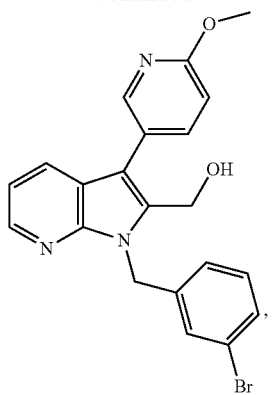
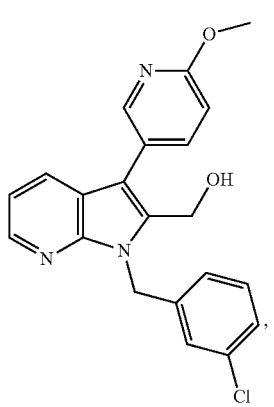
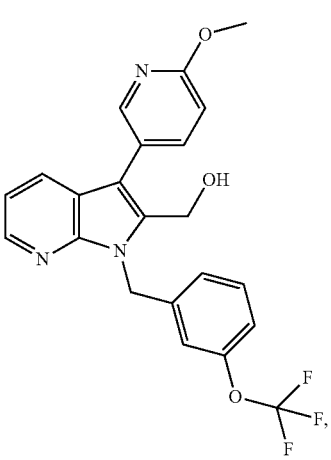
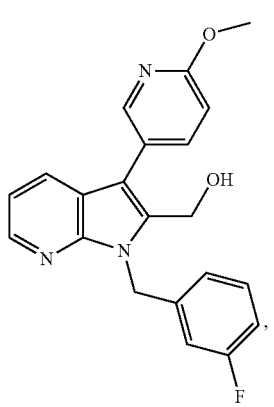
120
-continued
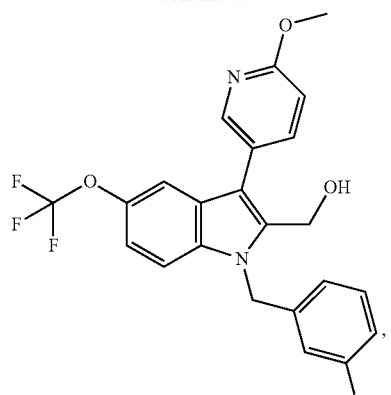
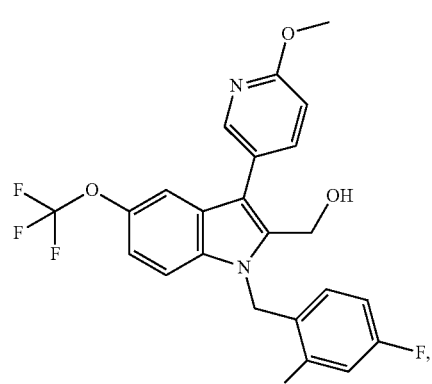
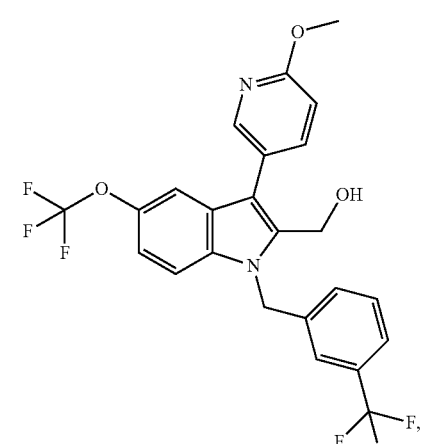
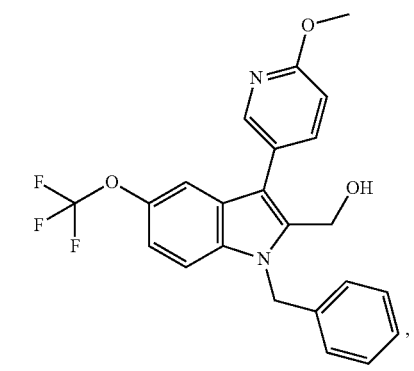

121
-continued
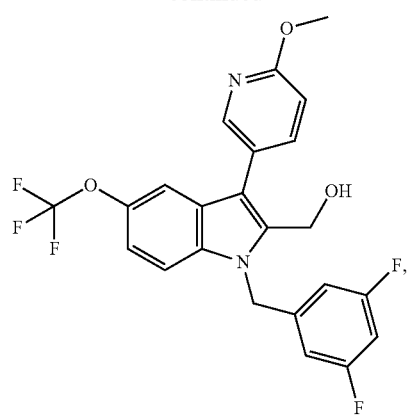
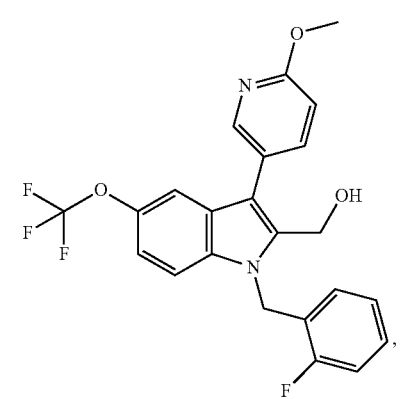
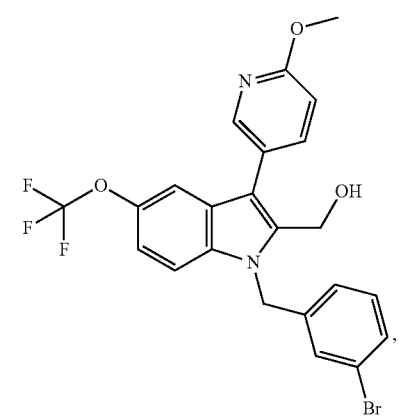
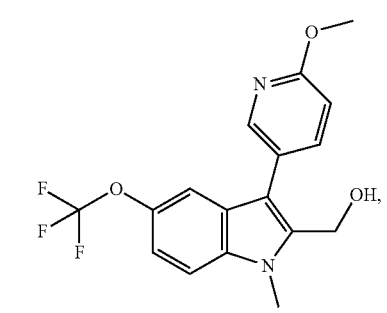
122
-continued
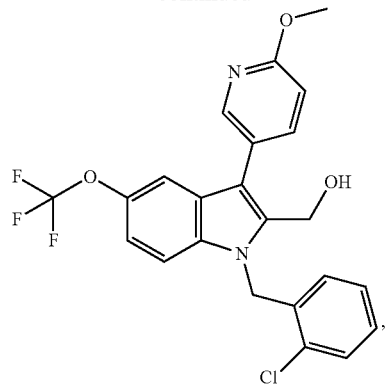
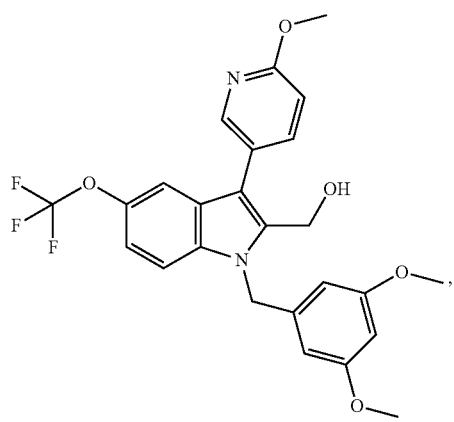
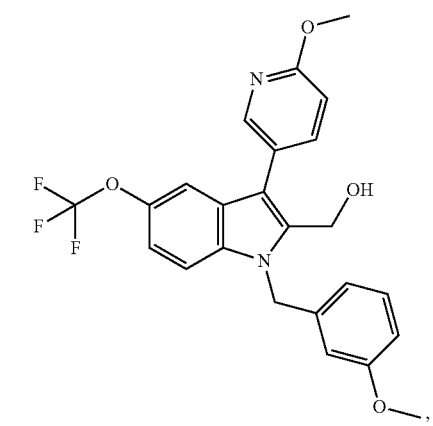
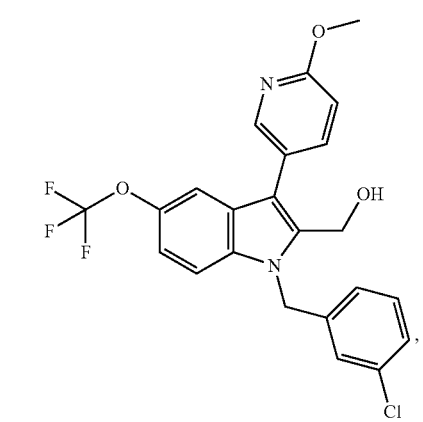

123
-continued
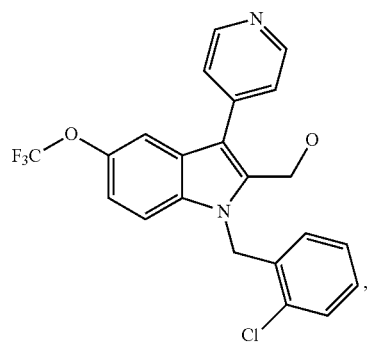
124
-continued
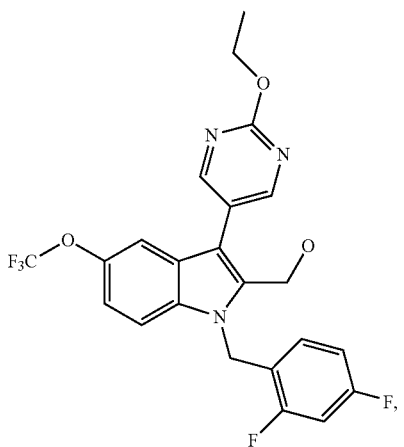
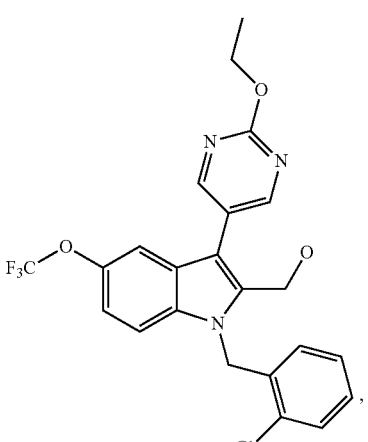
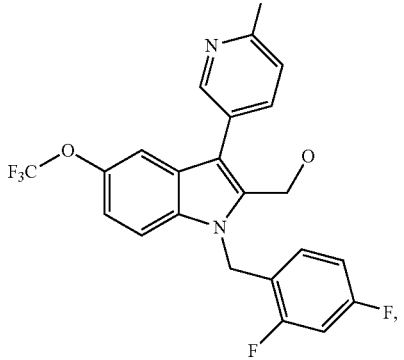
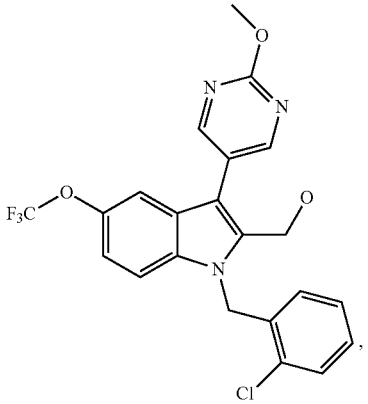

125
-continued
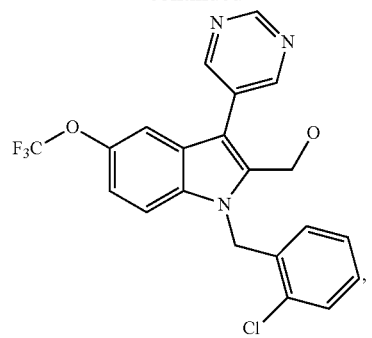
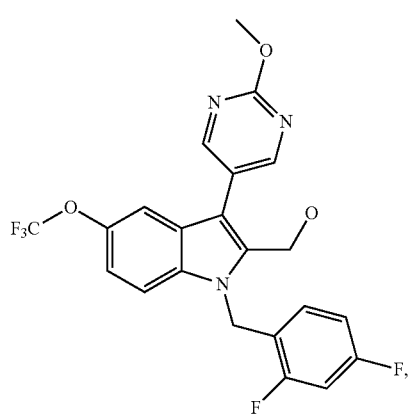
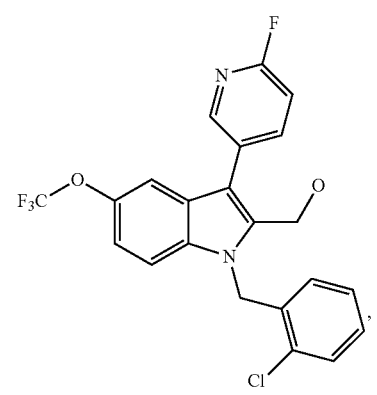
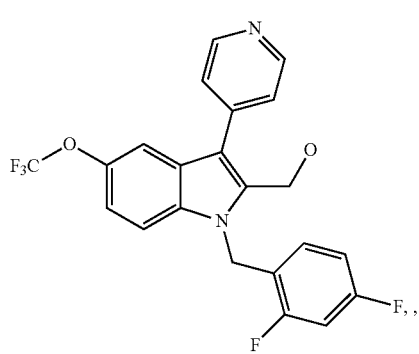
126
-continued
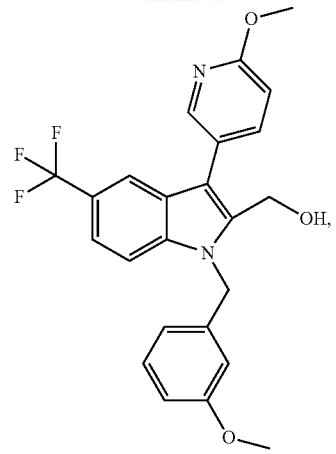
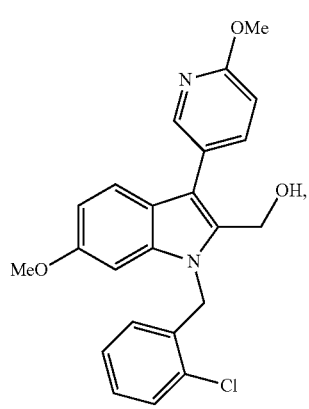
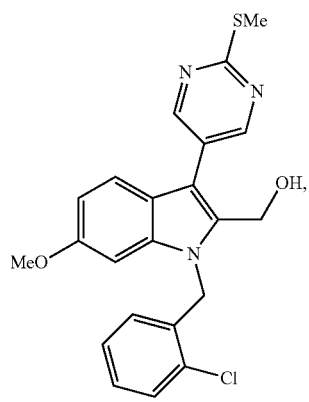
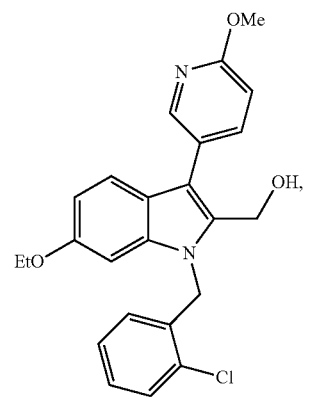

127
-continued
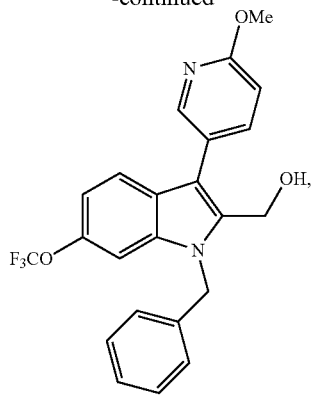
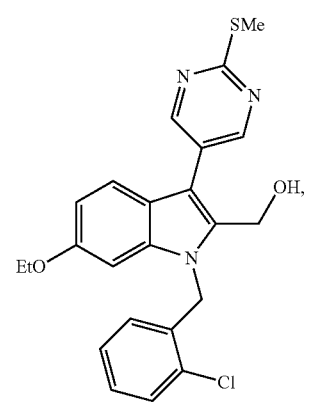
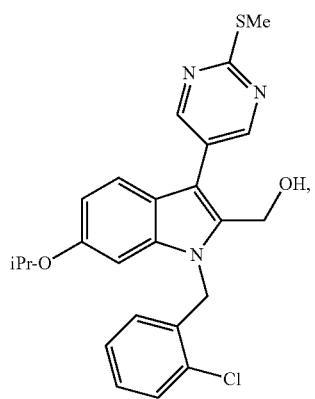
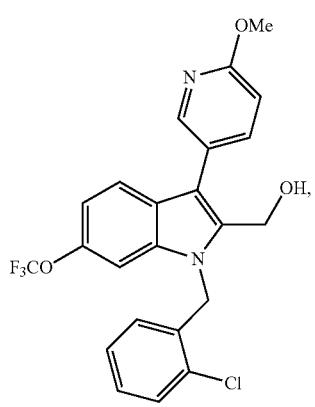
128
-continued
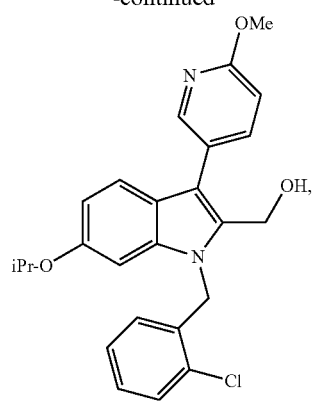
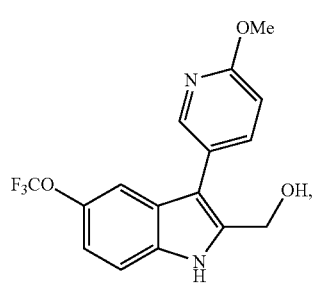
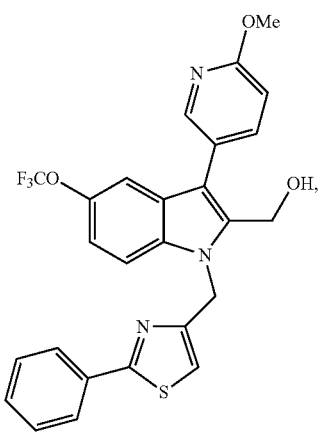
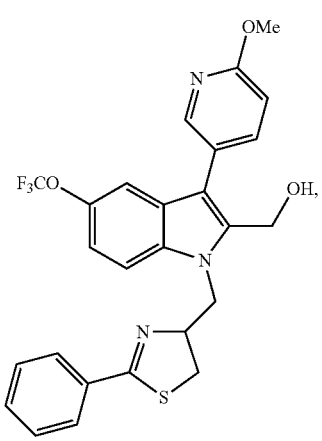

-continued
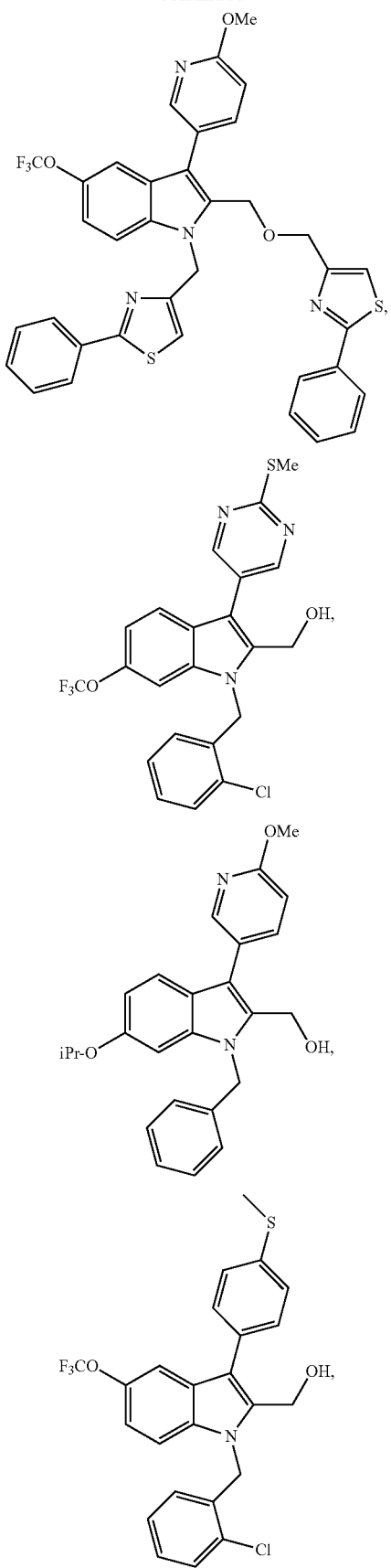
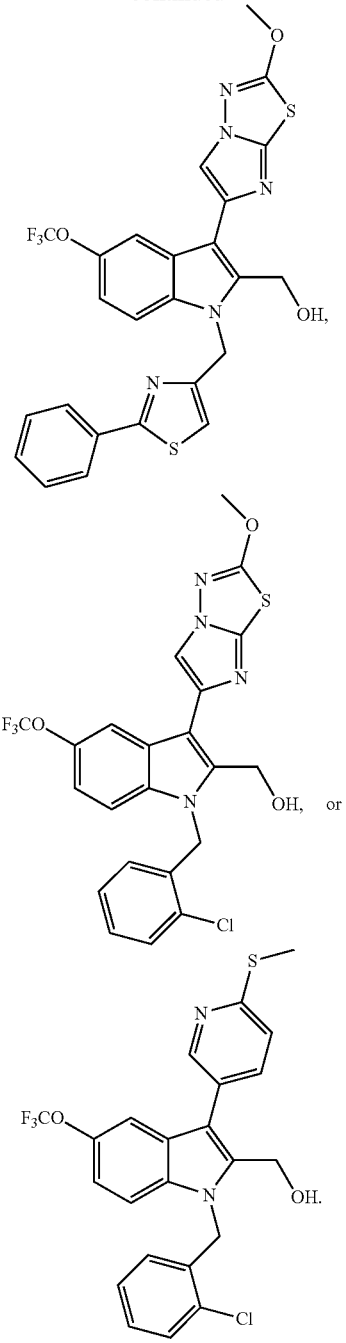
15. A composition comprising a compound having a structure represented by formula (I):
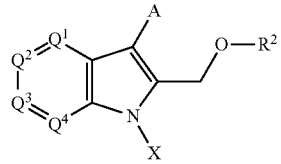
I.
wherein:
Q$^1$ is selected from N and CR$^{1a}$;
Q$^2$ is selected from N and CR$^{1b}$, or can optionally cyclize with Q$^3$ to form a C5 or C6 saturated heterocycle;

Q³ is selected from N and CR¹ᶜ, or can optionally cyclize with Q² to form a C5 or C6 saturated heterocycle;

Q⁴ is selected from N and CR¹ᵈ; and wherein 0, 1, or 2 of Q¹, Q², Q³, and Q⁴ are N;

R¹ᵃ, R¹ᵇ, R¹ᶜ, and R¹ᵈ, when present, are each independently selected from hydrogen, halogen, hydroxyl, cyano, $C_1$-$C_3$ alkyl sulfone, $C_1$-$C_3$ polyhaloalkyl sulfone, $C_1$-$C_6$ alkyl, $C_1$-$C_6$ haloalkyl, $C_1$-$C_6$ polyhaloalkyl, $C_1$-$C_6$ alkoxy, ($C_1$-$C_6$) alkoxy-($C_1$-$C_6$) alkyl, ($C_1$-$C_6$) alkylamino, ($C_1$-$C_6$) haloalkyl-oxy-($C_1$-$C_6$) alkyl, ($C_1$-$C_6$) polyhaloalkyl-oxy-($C_1$-$C_6$) alkyl, ($C_1$-$C_6$) polyhaloalkyl-($C_1$-$C_6$) alkoxy, and ($C_1$-$C_6$) dialkylamino; n is 0-5;

X is independently selected from optionally substituted CH₂-aryl, CH₂-heteroaryl, CH₂-biaryl, or

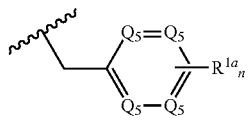

wherein:
Q⁵ is selected from N, CR¹ᵃ, and R¹ᵃ; and
n is 0-5;

R² is selected from hydrogen, $C_1$-$C_3$ alkyl, $C_1$-$C_3$ haloalkyl, and $C_1$-$C_3$ polyhaloalkyl, ($C_1$-$C_3$) polyhaloalkyl-oxy-($C_1$-$C_3$) alkyl, and ($C_1$-$C_3$) haloalkyl-oxy-($C_1$-$C_3$) alkyl, and A is optionally substituted and chosen from imidazolyl, oxadiazolyl, oxazolyl, pyrazinyl, pyrazolyl, pyridinyl, pyrimidinyl, thiadiazolyl, thiazolyl, imidazothiadiazolyl, imidazooxadiazole, imidazothiazole, thiazolotriazole, and triazolyl;

or a pharmaceutically acceptable salt, solvate, or polymorph thereof; and a pharmaceutically acceptable carrier.

16. The composition of claim 15, wherein:
X is selected from substituted or unsubstituted CH₂-aryl, CH₂-heteroaryl, CH₂-biaryl.

17. The composition of claim 15, wherein R² is hydrogen.

18. The composition of claim 15, wherein Q² is substituted with C—O—CF₃.

19. The composition of claim 15, wherein A is of the following formula;

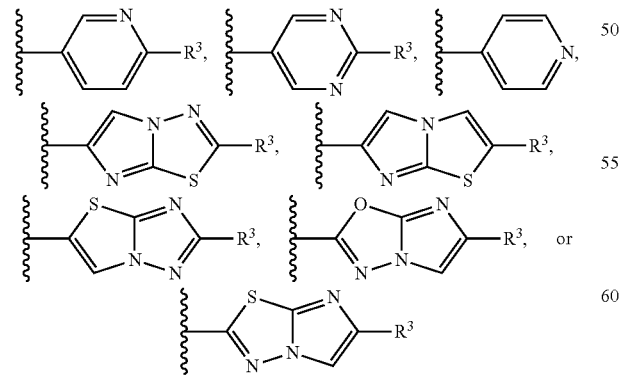

wherein:
R³ is selected from —O—CH₃, halogen, —S—CH₃, hydrogen, or —O—CH₂CH₃.

20. The composition of claim 15, (I), wherein Q² cyclizes with Q³ to form dioxolane.

21. The composition of claim 15, wherein X is optionally substituted benzyl or optionally substituted pyridinyl.

22. The composition of claim 15, wherein the compound is of the following formula:

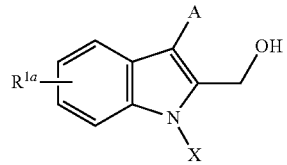

wherein:
X is CH₂—R⁴;
R⁴ is substituted or unsubstituted phenyl, pyridinyl, phenyldihydrothiazolyl or phenylthiazolyl.

23. The composition of claim 15, wherein the compound is of the following formula:

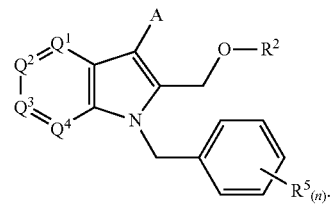

24. The composition of claim 23, wherein Q⁴ is N;
R⁵ is selected from hydrogen, Cl, Br, F, cyano, O—CF₃, —O—CH₃, or CF₃; and n is 0-2.

25. The composition of claim 23, wherein the compound is of the following formula:

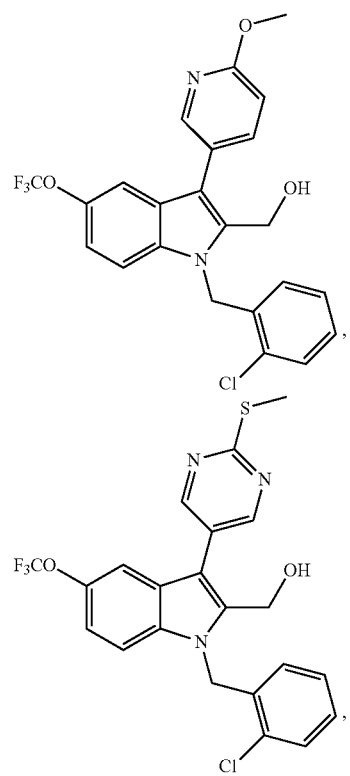

-continued

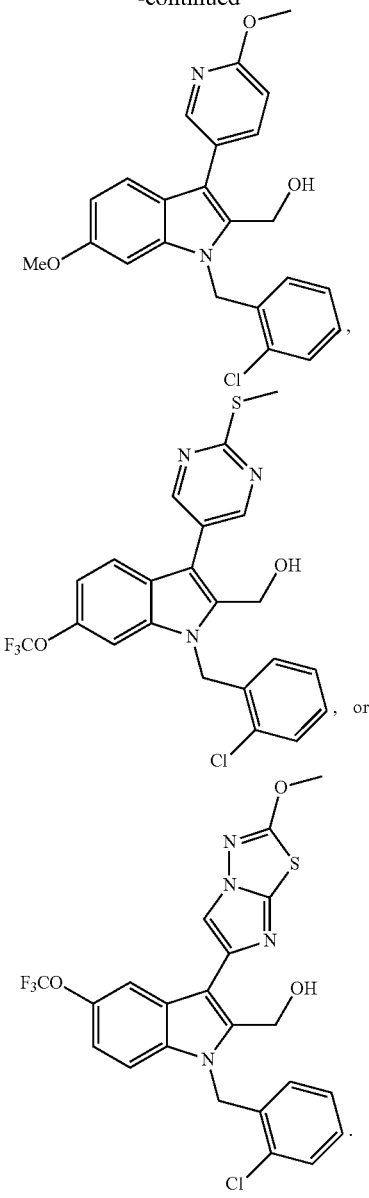

26. A method of preventing or treating thromboembolic disorder, comprising administering to a patient in need thereof an effective amount of a composition that includes a compound having a structure represented by formula (I):

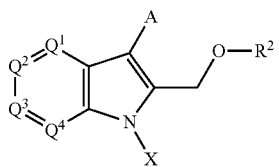

wherein:
Q$^1$ is selected from N and CR$^{1a}$;
Q$^2$ is selected from N and CR$^{1b}$, or can optionally cyclize with Q$^3$ to form a C5 or C6 saturated heterocycle;
Q$^3$ is selected from N and CR$^{1c}$, or can optionally cyclize with Q$^2$ to form a C5 or C6 saturated heterocycle;
Q$^4$ is selected from N and CR$^{1d}$; and wherein 0, 1, or 2 of Q$^1$, Q$^2$, Q$^3$, and Q$^4$ are N;
R$^{1a}$, R$^{1b}$, R$^{1c}$, and R$^{1d}$, when present, are each independently selected from hydrogen, halogen, hydroxyl, cyano, C$_1$-C$_3$ alkyl sulfone, C$_1$-C$_3$ polyhaloalkyl sulfone, C$_1$-C$_6$ alkyl, C$_1$-C$_6$ haloalkyl, C$_1$-C$_6$ polyhaloalkyl, C$_1$-C$_6$ alkoxy, (C$_1$-C$_6$) alkoxy-(C$_1$-C$_6$) alkyl, (C$_1$-C$_6$) alkylamino, (C$_1$-C$_6$) haloalkyl-oxy-(C$_1$-C$_6$) alkyl, (C$_1$-C$_6$) polyhaloalkyl-oxy-(C$_1$-C$_6$) alkyl, (C$_1$-C$_6$) polyhaloalkyl-(C$_1$-C$_6$) alkoxy, and (C$_1$-C$_6$) dialkylamino; n is 0-5;
X is independently selected from optionally substituted CH$_2$-aryl, CH$_2$-heteroaryl, CH$_2$-biaryl, or

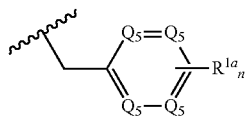

wherein:
Q$^5$ is selected from N, CR$^{1a}$, and R$^{1a}$; and
n is 0-5;
R$^2$ is selected from hydrogen, C$_1$-C$_3$ alkyl, C$_1$-C$_3$ haloalkyl, and C$_1$-C$_3$ polyhaloalkyl, (C$_1$-C$_3$) polyhaloalkyl-oxy-(C$_1$-C$_3$) alkyl, and (C$_1$-C$_3$) haloalkyl-oxy-(C$_1$-C$_3$) alkyl, and
A is optionally substituted and chosen from aryl or heteroaryl;
or a pharmaceutically acceptable salt, solvate, or polymorph thereof; and
a pharmaceutically acceptable carrier.

27. A method of inhibiting PAR-4 activity, comprising administering to a patient in need thereof an effective amount of a composition that includes a compound having a structure represented by formula (I):

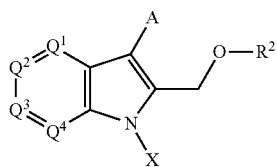

wherein:
Q$^1$ is selected from N and CR$^{1a}$;
Q$^2$ is selected from N and CR$^{1b}$, or can optionally cyclize with Q$^3$ to form a C5 or C6 saturated heterocycle;
Q$^3$ is selected from N and CR$^{1c}$, or can optionally cyclize with Q$^2$ to form a C5 or C6 saturated heterocycle;
Q$^4$ is selected from N and CR$^{1d}$; and wherein 0, 1, or 2 of Q$^1$, Q$^2$, Q$^3$, and Q$^4$ are N;
R$^{1a}$, R$^{1b}$, R$^{1c}$, and R$^{1d}$, when present, are each independently selected from hydrogen, halogen, hydroxyl, cyano, C$_1$-C$_3$ alkyl sulfone, C$_1$-C$_3$ polyhaloalkyl sulfone, C$_1$-C$_6$ alkyl, C$_1$-C$_6$ haloalkyl, C$_1$-C$_6$ polyhaloalkyl, C$_1$-C$_6$ alkoxy, (C$_1$-C$_6$) alkoxy-(C$_1$-C$_6$) alkyl, (C$_1$-C$_6$) alkylamino, (C$_1$-C$_6$)

haloalkyl-oxy-$(C_1$-$C_6)$ alkyl, $(C_1$-$C_6)$ polyhaloalkyl-oxy-$(C_1$-$C_6)$ alkyl, $(C_1$-$C_6)$ polyhaloalkyl-$(C_1$-$C_6)$ alkoxy, and $(C_1$-$C_6)$ dialkylamino; n is 0-5;

X is independently selected from optionally substituted $CH_2$-aryl, $CH_2$-heteroaryl, $CH_2$-biaryl, or

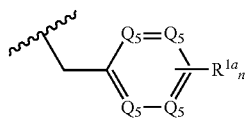

wherein:

$Q^5$ is selected from N, $CR^{1a}$, and $R^{1a}$; and n is 0-5;

$R^2$ is selected from hydrogen, $C_1$-$C_3$ alkyl, $C_1$-$C_3$ haloalkyl, and $C_1$-$C_3$ polyhaloalkyl, $(C_1$-$C_3)$ polyhaloalkyl-oxy-$(C_1$-$C_3)$ alkyl, and $(C_1$-$C_3)$ haloalkyl-oxy-$(C_1$-$C_3)$ alkyl, and A is optionally substituted and chosen from aryl or heteroaryl;

or a pharmaceutically acceptable salt, solvate, or polymorph thereof; and a pharmaceutically acceptable carrier.

* * * * *

UNITED STATES PATENT AND TRADEMARK OFFICE
CERTIFICATE OF CORRECTION

PATENT NO. : 9,572,794 B2
APPLICATION NO. : 14/820488
DATED : February 21, 2017
INVENTOR(S) : Hamm et al.

Page 1 of 1

It is certified that error appears in the above-identified patent and that said Letters Patent is hereby corrected as shown below:

In the Specification

Column 1, Line 5 should read:
Government Support
This invention was made with government support under grant numbers NS081669, HL084388, and HL081009 awarded by the National Institutes of Health. The government has certain rights in the invention.

Signed and Sealed this
Fourth Day of February, 2020

Andrei Iancu
*Director of the United States Patent and Trademark Office*